US012156904B2

(12) United States Patent
De Souza et al.

(10) Patent No.: US 12,156,904 B2
(45) Date of Patent: Dec. 3, 2024

(54) POLYPEPTIDES WITH ASPARAGINASE ACTIVITY, RELATED COMPOSITIONS, AND METHODS OF USE THEREOF

(71) Applicant: FUNDAÇÃO OSWALDO CRUZ, Manguinhos (BR)

(72) Inventors: Tatiana De Arruda Campos Brasil De Souza, Curitiba (BR); Nilson Ivo Tonin Zanchin, Curitiba (BR); Stephanie Bath De Morais, Curitiba (BR)

(73) Assignee: FUNDAÇÃO OSWALDO CRUZ, Rio de Janeiro (BR)

( * ) Notice: Subject to any disclaimer, the term of this patent is extended or adjusted under 35 U.S.C. 154(b) by 1140 days.

(21) Appl. No.: 16/963,173

(22) PCT Filed: Jan. 18, 2019

(86) PCT No.: PCT/BR2019/050017
§ 371 (c)(1),
(2) Date: Jul. 17, 2020

(87) PCT Pub. No.: WO2019/140501
PCT Pub. Date: Jul. 25, 2019

(65) Prior Publication Data
US 2021/0121544 A1 Apr. 29, 2021

(30) Foreign Application Priority Data
Jan. 18, 2018 (BR) ...................... BR1020180010336

(51) Int. Cl.
*A61K 38/50* (2006.01)
*A61P 35/02* (2006.01)
*C12N 15/66* (2006.01)

(52) U.S. Cl.
CPC .............. *A61K 38/50* (2013.01); *A61P 35/02* (2018.01); *C12N 15/66* (2013.01)

(58) Field of Classification Search
None
See application file for complete search history.

(56) References Cited

U.S. PATENT DOCUMENTS
2006/0088880 A1 4/2006 Williamson et al.

FOREIGN PATENT DOCUMENTS
CN 106434612 2/2017

OTHER PUBLICATIONS

Bush, L.A. et al. 2002. A novel asparaginase-like protein is a sperm autoantigen in rats. Molecular Reproduction and Development 62: 233-247; specif. pp. 233, 238 (Year: 2002).*

Belviso et al., "The human asparaginase enzyme (ASPG) inhibits growth in leukemic cells," PLoS One, May 24, 2017, 12(5):e017817414; 14 pp.
Li et al., "Uncoupling Intramolecular Processing and Substrate Hydrolysis in the N-Terminal Nucleophile Hydrolase hASRGL 1 by Circular Permutation," ACS Chem Biol, 2012, 7(11):1840-1847.
Nomme et al., "Elucidation of the Specific Function of the Conserved Threonine Triad Responsible for Human L-Asparaginase Autocleavage and Substrate Hydrolysis," J Mol Biol, Jun. 26, 2014, 426(13):2471-2485.
International Search Report issued Mar. 15, 2019, in PCT/BR2019/050017, including translation.
Written Opinion issued Mar. 15, 2019, in PCT/BR2019/050017.
American Cancer Society, Leukemia—Acute Lymphocytic (Adults), 2016, 48 pages.
Treatment of Acute Lymphoid Leukemia (ALL) in Children, Available online at: https://www.oncoguia.org.br/conteudo/tratamento-da-leucemia-linfoide-aguda-lla-em-criancas/3914/603/, Dec. 12, 2013, pp. 1-3.
Avramis et al., Asparaginase (Native ASNase or Pegylated ASNase) in the Treatment of Acute Lymphoblastic Leukemia, International Journal of Nanomedicine, vol. 1, No. 3, 2006, pp. 241-254.
Avramis, Asparaginases: Biochemical Pharmacology and Modes of Drug Resistance, Anticancer Research, vol. 32, No. 7, Jul. 2012, pp. 2423-2437.
Bansal et al., Hyperthermophilic Asparaginase Mutants with Enhanced Substrate Affinity and Antineoplastic Activity: Structural Insights on Their Mechanism of Action, The FASEB Journal, vol. 26, No. 3, Dec. 15, 2011, pp. 1-11.
Bohme et al., Isoaspartate Residues Dramatically Influence Substrate Recognition and Turnover by Proteases, Journal of Biological Chemistry, vol. 389, No. 8, Aug. 2008, pp. 1043-1053.
Brannigan et al., A Protein Catalytic Framework with an N-terminal Nucleophile is Capable of Self-Activation, Nature, vol. 378, Nov. 23, 1995, pp. 416-419.
Bush et al., "A Novel Asparaginase-Like Protein Is a Sperm Autoantigen in Rats," Mol Reproduct Dev, 2002, 62:(2):233-247.
Cantor et al., The Human Asparaginase-Like Protein 1 hASRGL1 is an Ntn-Hydrolase with β-aspartyl Peptidase Activity, Biochemistry, vol. 48, No. 46, Nov. 24, 2009, pp. 1-15.
Cario et al., Initial Leukemic Gene Expression Profiles of Patients with Poor in Vivo Prednisone Response Are Similar to Those of Blasts Persisting Under Prednisone Treatment in Childhood Acute Lymphoblastic Leukemia, Annals of Hematology, vol. 87, No. 9, Sep. 2008, pp. 709-716.

(Continued)

*Primary Examiner* — Adam Weidner
*Assistant Examiner* — Sharon M. Papciak
(74) *Attorney, Agent, or Firm* — Kilpatrick Townsend & Stockton LLP

(57) ABSTRACT

The present invention refers to polypeptides with asparaginase activity that have an increased rate of self-processing compared to human wild L-asparaginase (ASRGLI), resulting from a mutation in the ASRGLI glycine rich loop called HGG loop (Histidine 8-Glycine 9-Glycine 10). Polynucleotides that encode the polypeptides of invention are also described herein. Expression cassettes comprising said polynucleotides, expression vectors, host cells, pharmaceutical compositions, uses of the invention polypeptide in the manufacture of a preventive medicine or cancer treatment and methods to produce the polypeptide of invention and to prevent or treat cancer are also described.

16 Claims, 6 Drawing Sheets

Specification includes a Sequence Listing.

(56) References Cited

OTHER PUBLICATIONS

Carroll et al., Pediatric Acute Lymphoblastic Leukemia, American Society of Hematology, 2003, pp. 102-131.

Cooper et al., Treatment of Pediatric Acute Lymphoblastic Leukemia, Pediatric Clinics of North America, vol. 62, No. 1, Feb. 2015, pp. 1-15.

Dieterich et al., Gliap—A Novel Untypical L-asparaginase Localized to Rat Brain Astrocyte, Journal of Neurochemistry, vol. 85, Jun. 1, 2003, pp. 1117-1125.

Dolowy et al., Toxic and Antineoplastic Effects of L-Asparaginase, Study of Mice with Lymohoma and Normal Monkeys and Report on a Child with Leukemia, Cancer, vol. 19, No. 12, Mar. 16, 1966, pp. 1813-1819.

Dumon-Seignovert et al., The Toxicity of Recombinant Proteins in *Escherichia coli*: a Comparison of Overexpression in BL21(DE3), C41(DE3), and C43(DE3), Protein Expression and Purification, vol. 37, No. 1, Sep. 2004, pp. 203-206.

Evtimova et al., Identification of CRASH, a Gene Deregulated in Gynecological Tumors, International Journal of Oncology, vol. 24, Jan. 1, 2004, pp. 33-41.

Grantham et al., Codon Frequencies in 119 Individual Genes Confirm Corsistent Choices of Degenerate Bases According to Genome Type, Nucleic Acids Research, vol. 8, No. 9, May 1980, pp. 1893-1912.

Grosjean et al., Preferential Codon Usage in Prokaryotic Genes: the Optimal Codon-anticodon Interaction Energy and the Selective Codon Usage in Efficiently Expressed Genes, Gene, vol. 18, No. 3, Jun. 1982, pp. 199-209.

Grunberg-Manago, Messenger RNA Stability and Its Role in Control of Gene Expression in Bacteria and Phages, Annual Review of Genetics, vol. 33, Jan. 1, 1999, pp. 193-227.

Haas et al., Codon Usage Limitation in the Expression of HIV-1 Envelope Glycoprotein, Current Biology, vol. 6, No. 3, Mar. 1996, pp. 315-324.

Holm, Codon Usage and Gene Expression, Nucleic Acids Research, vol. 14, No. 7, Apr. 1986, pp. 3075-3087.

Hunger et al., Improved Survival for Children and Adolescents with Acute Lymphoblastic Leukemia Between 1990 and 2005: A Report From the Children's Oncology Group, Journal of Clinical Oncology, vol. 30, No. 14, May 10, 2012, pp. 1663-1669.

Ikemura, Correlation Between the Abundance of Yeast Transfer RNAs and the Occurrence of the Respective Codons in Protein Genes. Differences in Synonymous Codon Choice Patterns of Yeast *Escherichia coli* with Reference to the Abundance of Isoaccepting Transfer RNAs, Journal of Molecular Biology, vol. 158, No. 4, Jul. 1982, pp. 573-597.

Kane, Effects of Rare Codon Clusters on High-level Expression of Heterologous Proteins in *Escherichia coli*, Current Opinion in Biotechnology, vol. 6, No. 5, Oct. 1995, pp. 494-500.

Karamitros et al., Bacterial co-expression of the α and β Protomers of Human L-asparaginase-3: Achieving Essential N-terminal Exposure of a Catalytically Critical Threonine Located in the β-Subunit, Protein Expression and Purification, vol. 93, Jan. 2014, pp. 1-10.

Laemmli, Cleavage of Structural Proteins During the Assembly of the Head of Bacteriophage T4, Nature, vol. 227, No. 5259, Aug. 1970, pp. 680-685.

Li et al., Intramolecular Cleavage of the hASRGL1 Homodimer Occurs in Two Stages, Biochemistry, vol. 55, No. 6, Feb. 16, 2016, pp. 1-26.

Li et al., The Downregulation of Asparagine Synthetase Expression can Increase the Sensitivity of Cells Resistant to L-asparaginase, Leukemia, vol. 20, No. 12, Dec. 2006, pp. 2199-2201.

Lorenzi et al., A Curated Census of Autophagy-modulating Proteins and Small Molecules, Autophagy, vol. 10, No. 7, Jul. 2014, pp. 1316-1326.

Makrides, Strategies for Achieving High-level Expression of Genes in *Escherichia coli*, Microbiological Reviews, vol. 60, No. 3, Sep. 1996, pp. 512-538.

Michalska et al., Structural Aspects of L-asparaginases, their Friends and Relations, Acta Biochimica Polonica, vol. 53, No. 4, 2006, pp. 627-640.

Moghrabi et al., Results of the Dana-Farber Cancer Institute ALL Consortium Protocol 95-01 for Children with Acute Lymphoblastic Leukemia, Blood, vol. 109, No. 3, Feb. 1, 2007, pp. 896-905.

Moricke et al., Risk-adjusted Therapy of Acute Lymphoblastic Leukemia Can Decrease Treatment Burden and Improve Survival: Treatment Results of 2169 Unselected Pediatric and Adolescent Patients Enrolled in the Trial ALL-BFM 95, Blood, vol. 111, No. 9, May 2008, pp. 4477-4489.

Müller et al., Use of L-asparaginase in childhood ALL, Critical Reviews in Oncology/Hematology, vol. 28, No. 2, 1998, pp. 97-113.

Mullis et al., Specific Enzymatic Amplification of DNA in Vitro: the Polymerase Chain Reaction, Cold Spring Harbor Symposia on Quantitative Biology, vol. 51, Pt 1, 1986, pp. 263-273.

Nomme et al., Structures of Apo and Product-bound Human L-asparaginase: Insights Into the Mechanism of Autoproteolysis and Substrate Hydrolysis, Biochemistry, vol. 51, No. 34, Aug. 28, 2012, pp. 1-20.

Oinonen et al., Three-Dimensional Structure of Human Lysosomal Aspartylglucosaminidase, Nature Structural and Molecular Biology, vol. 2, No. 12, Dec. 1995, pp. 1102-1108.

Panosyan et al., Asparaginase Depletion Potentiates the Cytotoxic Effect of Chemotherapy Against Brain Tumors, Molecular Cancer Research, vol. 12, No. 5, May 2014, pp. 694-702.

Patel et al., A Dyad of Lymphoblastic Lysosomal Cysteine Proteases Degrades the Antileukemic Drug L-asparaginase, Journal of Clinical Investigation, vol. 119, No. 7, Jul. 2009, pp. 1964-1973.

Pejovic et al., Leukemias, Clinical Obstetrics and Gynecology, vol. 45, No. 3, Sep. 2002, pp. 866-878.

Pieters et al., L-asparaginase Treatment in Acute Lymphoblastic Leukemia: A Focus on Erwinia Asparaginase, Cancer, vol. 117, No. 2, Jan. 15, 2011, pp. 238-249.

Purwaha et al., Targeted Metabolomic Analysis of Amino Acid Response to L-asparaginase in Adherent Cells, Metabolomics, vol. 10, No. 5, Feb. 7, 2014, pp. 909-919.

Richards et al., Asparagine Synthetase Chemotherapy, Annual Review of Biochemistry, vol. 75, 2006, pp. 1-32.

Rose-Inman et al., Acute Leukemia, Emergency Medicine Clinics of North America, vol. 32, No. 3, Aug. 2014, pp. 579-596.

Roth et al., Recombinant Erwinia carotovora L-Asparaginase II Production in *Escherichia coli* FED-Batch Cultures, Brazilian Journal of Chemical Engineering, vol. 30, No. 2, Apr.-Jun. 2013, pp. 245-256.

Rytting, Role of L-asparaginase in Acute Lymphoblastic Leukemia: Focus on Adult Patients, Blood and Lymphatic Cancer: Targets and Therapy, Jun. 29, 2012, pp. 117-124.

Sarkar et al., Restriction-site PCR: a Direct Method of Unknown Sequence Retrieval Adjacent to a Known Locus by Using Universal Primers, Polymerase Chain Reaction Methods and Applications, vol. 2, No. 4, May 1993, pp. 318-322.

Schalk et al., Structural and Kinetic Characterization of Guinea Pig L-Asparaginase Type III, Biochemistry, vol. 53, No. 14, Mar. 26, 2014, pp. 2318-2328.

Sharp et al., Codon Usage and Genome Evolution, Current Opinion in Genetics and Development, vol. 4, No. 6, Dec. 1994, pp. 851-860.

Sircar et al., Integrative Molecular Profiling Reveals Asparagine Synthetase Is a Target in Castration-Resistant Prostate Cancer, The American Journal of Pathology, vol. 180, No. 3, Mar. 2012, pp. 895-903.

Song et al., Asparaginase Induces Apoptosis and Cytoprotective Autophagy in Chronic Myeloid Leukemia Cells, Oncotarget, vol. 6, No. 6, Jan. 8, 2015, pp. 3861-3873.

Su et al., Free Glycine Accelerates the Autoproteolytic Activation of Human Asparaginase, Chemistry and Biology, vol. 20, No. 4, Apr. 18, 2013, pp. 1-18.

Sugimoto et al., Cloning and Expression of cDNA Encoding Rat Liver 60-kDa Lysophospholipase Containing an Asparaginase-like Region and Ankyrin Repeat, Journal of Biological Chemistry, vol. 273, No. 20, May 15, 1998, pp. 12536-12542.

Towbin et al., Electrophoretic Transfer of Proteins From Polyacrylamide Gels to Nitrocellulose Sheets: Procedure and Some Applications,

(56) References Cited

OTHER PUBLICATIONS

Proceedings of the National Academy of Sciences of the United States of America, vol. 76, No. 9, Sep. 1979, pp. 4350-4354.

Triglia et al., A Procedure for in Vitro Amplification of DNA Segments That Lie Outside the Boundaries of Known Sequences, Nucleic Acids Research, vol. 16, No. 16, Aug. 1988, 1 page.

Ueno et al., Cell Cycle Arrest and Apoptosis of Leukemia Cells Induced by L-Asparaginase, Leukemia, vol. 11, No. 11, Nov. 1997, pp. 1858-1861.

Wain-Hobson et al., Preferential Codon Usage in Genes, Gene, vol. 13, No. 4, May 1981, pp. 355-364.

Willems et al., Inhibiting Glutamine Uptake Represents an Attractive New Strategy for Treating Acute Myeloid Leukemia, Blood, vol. 122, No. 20, Nov. 14, 2013, pp. 3521-3532.

Yu et al., L-Asparaginase Inhibits Invasive and Angiogenic Activity and Induces Autophagy in Ovarian Cancer, Journal of Cellular and Molecular Medicine, vol. 16, No. 10, Oct. 2012, pp. 2369-2378.

Zhang et al., Targeting Asparagine and Autophagy for Pulmonary Adenocarcinoma Therapy, Applied Microbiology and Biotechnology, vol. 100, No. 21, Nov. 2016, pp. 9145-9161.

\* cited by examiner

POLYPEPTIDES WITH ASPARAGINASE ACTIVITY, RELATED COMPOSITIONS, AND METHODS OF USE THEREOF

FIELD OF INVENTION

This invention relates to the field of oncology and biotechnology. More specifically, this invention relates to polypeptides with asparaginase activity useful in the prevention and treatment of cancer.

SEQUENCE LISTING

This application contains a Sequence Listing which has been submitted in ASCII format via EFS-Web and is hereby incorporated by reference in its entirety. Said ASCII copy, created on Aug. 28, 2020, is named K110789_1020US_PCT_Sequence_Listing_ST25.txt and is 19.6 KB (20,126 bytes) in size.

BACKGROUND OF THE INVENTION

Leukemia is a malignant disease characterized by the excessive and unregulated proliferation of abnormal cells in the bone marrow, which are cells carrying an accumulation of mutations that prevent them from completing their differentiation, replace normal hematopoietic cells. Among the main consequences of leukemia on an individual are increased risk for anemia and bleeding, and the increased susceptibility to contraction of infections. In addition, leukemic cells can invade several other tissues through the circulation. Without effective treatment, leukemia is lethal.

According to clinical and pathological parameters, leukemia is subdivided in two manners. The first division is based on time of development and includes the acute and chronicle forms. The second is related to the type of cell affected. Lymphoid and myeloid leukemias are characterized by neoplastic changes in lymphoid and myeloid progenitor cells, respectively.

The world scenario in 2012 showed that 2.5% of all types of cancer are leukemia, totaling approximately 352,000 new cases this year. With a high mortality rate, 265,000 deaths from leukemia were expected in the world that same year. In Brazil, an estimated 10,070 new cases out of all types of leukemia were reported for the year 2016, with acute lymphoid leukemia (ALL) being the most common cancer in childhood. This disease corresponds to 30% of all malignant neoplasms in children aged 0 to 14 years. (AMERICAN CANCER SOCIETY, 2016).

The current treatment of ALL is composed of three phases. The protocol describing the stages of treatment was developed by the European group Berlin-Frankfurt-Munich (BFM) and has been used by INCA's Hematology System since 1982 (INCA, 2001). This protocol is based on the stratification of patients according to the different risk groups of recurrence of the disease. Patients in the low-risk group are those aged between 1 and 10 incomplete years, with a leukocyte count of less than 50,000/µL blood. Chromosomal or genetic changes in lymphocytes, variation in cell count after treatment initiation, presence of leukemic cells in the cerebrospinal fluid and the origin of leukemic cells (whether T or B lymphocytes) are factors that can also affect the prognosis (US Cancer Institute, 2014). In addition, this protocol combines different chemotherapy drugs in order to reduce patient resistance.

The first phase is called induction, lasts from one to three months, and aims to achieve remission, when the cell counts in the blood return to normal and no leukemic cells are found in the bone marrow. A chemotherapeutic, steroid and asparaginase enzyme are used for induction. The second phase is consolidation, where an attempt is made to completely eliminate the remaining leukemic cells by preventing them from becoming resistant. For this purpose several chemotherapeutic drugs are used and asparaginase. This is the most intense phase of the treatment, lasting two months. After the complete remission of the leukemic cells, the maintenance phase begins, which can last from two to three 5 years and makes use of chemotherapy and steroids. (INCA, 2001; MÖRICKE et al., 2008; INSTITUTO ONCOGUIA, 2013).

In the last 40 years there have been notable advances in the treatment of infant ALL, resulting in a survival rate of up to 90% for patients (AMERICAN CANCER SOCIETY, 2016). The introduction of asparaginase in the treatment at the end of the 1970s contributed to an increase of at least 15% in the survival rate. However, significant challenges remain, such as the development of therapeutic approaches with lower toxicity.

The efficacy of the use of asparaginase enzyme in the treatment of ALL is based on the deficiency presented by most leukemic cells: absence or reduction of asparagine synthase protein expression. Asparagine synthase performs the conversion from aspartate to asparagine. Being unable to synthesize asparagine again, leukemic cells are dependent on circulating asparagine. Tumor cells, especially in ALL, require a large amount of asparagine to maintain their abnormal growth characteristic of these malignant diseases. For this reason, the use of asparaginase against ALL becomes advantageous. Intramuscular or intravenous injection of asparaginase causes rapid depletion of the amino acid in plasma, leading to a reduction in the metabolism of leukemic cells and ultimately to death by apoptosis, while normal cells maintain their functions by being able to synthesize asparagine. Thus, asparaginase has a selective effect on neoplastic cells, unlike a chemotherapeutic agent, for example, which affects the proliferation process of both cancerous and normal cells.

Asparagine is a non-essential amino acid important for the growth and development of all cells both healthy and neoplastic. By acting on protein biosynthesis, its depletion harms cell proliferation (AVRAIVIIS, 2012). The reduction of the circulating concentration of asparagine from 50 µM to 3 µM or less during treatment with asparaginase (AVRAMIS, 2012) prevents leukemic cells from continuing the cell cycle by activating apoptosis signaling. This is in line with evidence that depletion of an amino acid can lead to the induction of apoptosis or autophagia (SONG et al., 2015). In other types of cancer (ovarian cancer, chronic myeloid leukemia, and pulmonary adenocarcinoma), asparaginase has been reported to induce not only apoptosis, but also autophagy, given that asparagine acts as a negative modulator of this process.

Despite its primary use in the treatment of ALL, asparaginase has therapeutic potential for use in other types of cancer, such as acute myeloid leukemia (WILLEMS et al., 2013), ovarian cancer (LORENZI et al., 2014; YU et al., 2012; PURWAHA et al., 2014), brain cancer, prostate cancer, pulmonary adenocarcinoma (ZHANG et al., 2016), non-Hodgkin's lymphoma, chronic lymphoid leukemia, and sarcomas such as lymphosarcoma, reticulosarcoma and melanosarcoma.

Currently, three asparaginases are used in the therapy of ALL: the native L-asparaginase II of *Escherichia coli*, a PEGuilated form of this enzyme, and the isolated L-asparaginase of *Erwinia chrysanthemi*. The selection of asparaginase that will compose the chemotherapy regimen depends on the country in which the treatment is performed. The choice of enzyme version to be used prioritizes the reduction of side effects and maintaining the effectiveness of the treatment. In Brazil, *E. coli* L-asparaginase II is used as first choice (MÖRICKE et al., 2008; PIETERS et al., 2011).

*E. coli* L-asparaginase II is the most toxic and immunogenic among the three available. Even in the last BFM protocol update there was a 50% reduction in the dose of this enzyme due to its side effects. After administration, *E. coli* L-asparaginase II is soon recognized by the cells of the immune system as it does not diffuse into extracellular space. Once the immune response is activated, the enzyme will have its action neutralized. In 60% of the patients a hypersensitivity reaction associated with the inactivation of the drug is generated. However, the antibodies produced against *E. coli* L-asparaginase II are not always accompanied by the characteristic symptoms of a hypersensitivity reaction (anaphylaxis, edema, serum disease, bronchospasm, urticaria and rash, itching and swelling of the extremities, erythema), in approximately 30% of patients a silent inactivation occurs (PIETERS et al., 2011; AVRAMIS, 2012).

PEGuilded enzyme and *E. chrysanthemi* isolate are indicated as substitutes in these cases of hypersensitivity and/or inactivation. PEG-asparaginase is relatively less immunogenic. However, its administration after treatment with the native enzyme may result in silent inactivation because of a cross-reaction with anti paraginase antibodies already present in the patient. *E. chrysanthemi* L-asparaginase largely solves the problem of hypersensitivity since the chances of developing antibodies against this enzyme are 12-20%. However, it has a shorter half-life and studies report a significantly higher number of patients who do not achieve complete remission of leukemic cells (PIETERS et al., 2011; RYTTING, 2012; AVRAMIS, 2012).

In addition to the effects resulting from the arousal of the immune response, the administration of multiple doses of asparaginase can generate toxic effects. The high toxicity of bacterial asparaginases is related to their hydrolytic non-specificity, leading also to the depletion of glutamine, which is converted to glutamate and ammonia by these enzymes. This non-specific hydrolysis is related to most of the side effects, such as liver disease, acute pancreatitis, hyperglycemia, glucosuria, ketoacidosis, central nervous system disorders, hypoalbuminemia, hypofibrinonemia, hypercoagulation, among other dysfunctions. It has been described that glutamine deprivation can activate intracellular mechanisms that reach the mitochondria and activate the apoptosis pathways, but this does not alleviate the toxic effects generated by glutamine hydrolysis and may still induce growth factor expression (AVRAMIS, 2012).

In addition to selectively leading leukemic cells to death, asparaginase enhances the antileukemic effect of steroids by further improving treatment outcomes. Therefore, research with asparaginase has sought the production of an enzyme with a high affinity for asparagine and a long half-life. These characteristics can be found in a human asparaginase enzyme, an alternative treatment option to bacterial asparaginases.

The inclusion of human L-asparaginase in the treatment of acute lymphoid leukemia could solve many of the problems faced with bacterial enzymes. However, it is a challenging solution because the human enzyme is only active after a self-binding stage, which presents a low in vitro efficiency, reducing its enzyme activity.

Studies on human-asparaginase (ASRGL1) have intensified in recent years due to the interest in its potential therapeutic use in some types of cancer, especially in ALL cases.

As a human protein, ASRGL1 can drastically reduce the immunogenicity of treatment; it meets the requirement of high thermal stability essential for drugs; it has a high affinity for asparagine and does not yet have glutaminase activity, ASRGL1 is unable to hydrolyze glutamine, its specificity being asparagine greater than other substrates (CANTOR et al., 2009).

The great challenge regarding the use of ASRGL1 in the therapeutic protocol of ALL lies in its enzymatic activity. The clinical prerequisite for the KM of an asparaginase protein is a low value in the micromolar order, while bacterial asparaginases fulfill this requirement, in vitro, hASRGL1 has a KM in the order of millimolar. The bacterial asparaginases used to treat ALL are from a different sub-family than human protein; while ASRGL1 belongs to the subfamily of the plant-type L-asparaginases, the bacterial ones belong to the bacterial-type, which do not have the need to undergo self-processing to become active (CANTOR et al., 2009).

As self-processing is a crucial event for enzyme activity and it has been demonstrated that kinetic activity is proportional to the self-processing rate, the low enzyme activity of ASGRL1 is understood to be due to the autocatalysis mechanism. Advances in genetic engineering have allowed various modifications to be made in order to increase the efficiency of in vitro self-processing, but without yet achieving success.

The auto cleavage mechanism starts with a proton acceptor solution from the T168 hydroxyl group. After deprotonation, T168 (with increased nucleophilic character) attacks the carbonyl group of G167 forming a covalent bond that will be hydrolyzed. The complete cleavage between the two residues leaves the amino grouping of T168 free to catalyze the hydrolysis of asparagine (SU et al., 2013). It is observed that the essential residue T168 of ASRGL1 plays a double role: first, its lateral chain is necessary for the autocleavage reaction. Secondly, with the breakdown of the peptide bond between G167 and T168, the T168-free amino group participates in the catalysis of asparagine hydrolysis.

Understanding the exact mechanism of ASRGL1 self-processing is essential to achieve a solution for low in vitro activity on the substrate. However, biochemical, and structural studies of the human enzyme have proven challenging, since the recombinant proteins generated for study are a mixture of the unprocessed (inactive) states and processed (active). Thus, the low activation rate (only 50% self-processing is achieved with the wild enzyme) makes both structural and enzymatic characterization difficult (CANTOR et al., 2009; LI et al., 2012).

In inactive protein, the distance between T168 hydroxyl and G167 carbonyl is 4.0 Å, which does not favor the chemical events necessary for self-processing, showing the need for a conformational change to cleavage (NOMIVIE et al., 2012). The inactivation of self-processing through the T168A mutation has caused a large increase in the thermal stability of the mutant protein ($\Delta TM=10°$ C.) . . . giving evidence of a steric voltage activation mechanism. This tension is due to the orientation of T168 in inactive protein. The electrons in your methyl grouping are very close to the hydroxyl of this residue, creating repulsive forces and unfavorable interactions. The self-processing causes a relaxation in the T168 lateral chain, bringing the T168 hydroxyl closer to the active site, since the distance between this hydroxyl and the amino grouping of T168 is reasonable 2.7 Å (LI et al., 2012).

The conformational change in the auto cleavage region can be facilitated by glycine 9 (G9) (NOMIVIE et al., 2012). The comparison between ASRGL1 structures before and after processing indicates a 180° rotation of the G9 carboxyl group (FIG. 1.10 B). This change in G9 conformation was also observed in the enzyme asparaginase type III of guinea pig 47 and can promote the repositioning of G167 (NOMIVIE et al., 2012) in order to bring it closer to T168 and encourage auto cleavage (NOMIVIE et al., 2012; LI et al., 2012).

G9 is part of a glycine rich loop called the HGG loop (Histidine 8-Glycine 9-Glycine 10). This loop is strongly conserved (~100%) throughout the phylogeny of L-asparaginases plant-type (LI), 2012).

LI et al., 2012 analyzed mutations in ASRGL1 HGG loop residues, particularly glycine 9 (G9) and glycine 10 (G10), to alanine, which resulted in reduced auto-processing rate (6 and 30 times, respectively) and kinetic activity (14 and 50 times, respectively).

LI et al., 2016 also evaluated variants of ASRGL1 with mutations in asparagine residues (N62), threonine 186 (T186) and threonine 219 (T219) for the auto-processing rate and to catalytic activity compared to wild ASRGL1. In Nomme et al., 2016, mutations in the ASRGL1 threonine 168 (T168) and threonine 219 (T219) waste were also studied with respect to the auto-processing rate and to catalytic activity compared to wild ASRGL1. Although some of these variants showed an increase in catalytic activity, none of the mutations performed resulted in an increase in the self-processing rate, All the mutations generated in different waste so far have helped to understand the mechanistic bases of ASRGL1 operation, but all have failed to increase their auto-processing rate and its hydrolytic activity on asparagine.

In this context, the present invention describes polypeptides with asparaginase activity, variants of the human L-asparaginase enzyme, useful in the treatment of cancer, which have lower side effects due to their low toxicity and immunogenicity compared to bacterial enzymes used therapeutically. These and other advantages of invention, as well as the additional inventive features joined to the same inventive concept, will be evident in the description of the invention provided in this document.

SUMMARY OF THE INVENTION

This invention aims to provide a polypeptide with asparaginase activity that solves the main state of the art problems listed above.

In a first aspect, the present invention provides a polypeptide with asparaginase activity selected from the group consisting of:
(i) a polypeptide that has an increased rate of auto-processing compared to human L-asparaginase in the wild presented in SEQ ID NO: 1;
(ii) a polypeptide comprising the amino acid sequence having at least 90% identity with the sequences of any of the SEQ ID Nos: 3-5;
(iii) a polypeptide in which the amino acid glycine at position 10 of the SEQ ID NO: 1 is replaced by an amino acid selected from the group consisting of glutamic acid, aspartic acid and histidine;
(iv) a polypeptide comprising the amino acid sequence presented in SEQ ID NO: 3-5; e
(v) a polypeptide of (i) to (iv) comprising one or more conservative amino acid substitutions.

In a second aspect, this invention provides a polynucleotide that encodes a polypeptide with asparaginase activity as above defined.

In a third aspect, this invention provides an expression cassette comprising a polynucleotide as defined above operationally linked to a promoter and to a transcription terminator.

In a fourth aspect, an expression vector comprising a polynucleotide, or an expression cassette as defined above is also provided.

In a fifth aspect, the present invention provides a host cell comprising an expression cassette or an expression vector as defined above.

In a sixth aspect, a pharmaceutical composition is provided which comprises a polypeptide of the invention and a pharmaceutically acceptable carrier or excipient.

In a seventh aspect, the use of the invention polypeptide is provided in the manufacture of a medicine for cancer prevention or treatment.

In an eighth aspect, this invention provides a method for producing a polypeptide with asparaginase activity, comprising the steps of: (a) providing a transformed host cell; (b) cultivating that cell under conditions conducive to polypeptide production; and (c) isolating that polypeptide from that cell or the surrounding culture medium.

In a ninth aspect, a method is provided to prevent or treat cancer, including administering a therapeutically effective amount of the polypeptide with asparaginase activity to an individual in need of such prevention, or treatment.

DEFINITIONS

Figure 1:
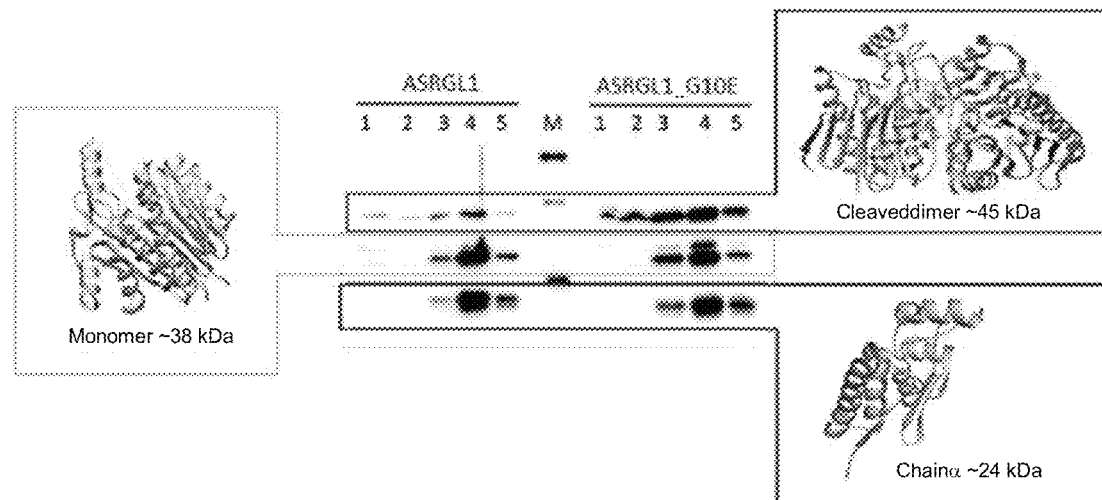
FIG. 1 shows a Western Blot assay of ASRGL1 and ASRGL1_G10E purified by affinity chromatography [M—Molecular weight marker (110, 48 and 25 kDa); 1—Flow through; 2—Elution with 50 mM imidazole; 3—Elution with 100 mM imidazole; 4—Elution with 500 mM imidazole; 5—Nickel resin].

To ensure a better understanding of the scope of the invention, without being a limiting factor, the technical terms of the related areas of technology as used in the present invention, are defined below.

"Comprising" or variations such as "comprise", "that comprises" or "comprised of" are used throughout the specification and claims in an inclusive sense, i.e., to specify the presence of the determined resources, but not to exclude the presence or addition of additional resources that may materially improve the operation or the usefulness of any of the terms of the invention unless the context requires otherwise due to the of the language of expression or implication required.

"consists essentially of" and variations such as "consist essentially of" or "consisting essentially of", as used throughout the specification, and claims, indicate the inclusion of any elements or group of elements referred and the optional inclusion of other elements, of a similar or different nature to the elements referred, that do not materially alter the basic or innovative properties of the material claimed.

The terms "nucleic acid" and "polynucleotide" are used interchangeably, and refer to RNA and DNA. Polynucleotides can be single or double tape. Non-limiting examples of polynucleotides include genes, gene fragments, exons, introns, messenger RNA, siRNA, miRNA, complementary DNA, genomic DNA, synthetic DNA, recombinant DNA, cassettes, vectors, probes and initiators. The term "recombinant DNA" refers to any artificial nucleotide sequence that results from the combination of DNA sequences of different origins.

The term 'degenerated nucleotide sequence' denotes a nucleotide sequence comprising one or more degenerated codons when compared with a reference nucleic acid molecule encoding a given polypeptide. Degenerated codons contain different nucleotide triplets, but encode the same amino acid residue (e.g., GAU and GAC both encode Asp).

The term "therapeutically effective amount" refers to an amount of protein or polypeptide that provides activity against cancer, when given in accordance with the dose and via appropriate administration.

The term 'pharmaceutically acceptable carriers or excipients' refers to ingredients that are compatible with other ingredients contained in pharmaceutical preparations and which have no therapeutic effect and are not harmful to humans or animals.

"Chemotherapeutic agent" is a chemical compound useful in cancer treatment. The classes of chemotherapeutic agents include, but are not limited to: alkylating agents, antimetabolites, kinase inhibitors, antifuse poison plant alkaloids, cytoxic/antitumor antibiotics, topoisomerase inhibitors, photosensitizers, antiestrogens and selective estrogen receptor modulators (SERMs), antiprogesterones, estrogen receptor descending regulators (ERDs), estrogen receptor antagonists, luteinizing hormone release agonists, antiandrogens, aromatase inhibitors, EGFR inhibitors, inhibitors of VEGF, antisense oligonucleotides that inhibit the expression of genes involved in abnormal cell proliferation or tumor growth. Chemotherapeutic agents useful in the treatment methods of this invention include cytostatic and/or cytotoxic agents.

The term "individual" refers to human beings and animals. Preferably the individual is a human being.

The term 'identity' is defined as the degree of equality between DNA or amino acid sequences when nucleotide by nucleotide or amino acid by amino acid is compared with a reference sequence.

The term "percentage of sequence identity" refers to comparisons between polynucleotides or polypeptides and is determined by two ideally aligned sequences, under certain comparison parameters. This alignment can comprise gaps (spaces), generating intervals when compared to the reference sequence, that facilitate a proper comparison of them. In general, the calculation of the percentage of identity takes into account the number of positions where the same nucleotide or amino acid occurs in the sequences compared to the reference sequence and is performed through several algorithms for comparing sequences and programs known in the state of the art. Such algorithms and programs include, but are not limited to, TBLASTN, BLASTP, FASTA, TFASTA, CLUSTALW, FASTDB.

The term "Polymerase Chain Reaction" or PCR refers to a method in which a nucleic acid fragment is amplified as described in U.S. Pat. No. 4,683,195. Generally, the information contained at the 5' and 3' ends of the sequence of interest is used for the design of the initiating oligonucleotides or primers they cover, around 8 synthetic nucleotides. These primers have sequences complementary to the sequence to be amplified. PCR can be used to amplify RNA sequences, DNA or cDNA.

An "expression cassette" refers to a nucleic acid construction comprising a coding region and a regulatory region, operationally linked, when introduced into a host cell, results in the transcription and/or translation of an RNA or polypeptide, respectively. Generally, an expression cassette is made up or understood by a promoter that allows the transcription to begin, a nucleic acid according to the invention, and transcription terminator. The expression "operationally linked" indicates that the elements are combined in such a way that the coding sequence expression is under the control of the transcriptional promoter and/or signal peptide. Typically, the promoter sequence is placed upstream of the gene of interest, at a distance from the gene of interest compatible with the control of the expression. Similarly, the signal peptide sequence is usually merged upstream of the gene sequence of interest, and in phase with this, and downstream of any promoter. Spacing sequences may be present between the regulatory elements and the gene as they do not prevent expression and/or sorting. In a performance mode, the said expression cassette comprises at least one activation sequence "enhancer" linked operationally to the promoter.

The term "vector" refers to nucleic acid molecules designed to transport, transfer and/or store genetic material, as well as express and/or integrate genetic material into the host cell's chromosomal DNA, such as plasmids, cosmids, artificial chromosomes, bacteriophages and other viruses. The vector usually consists of at least three basic units, the source of replication, a selection marker and the multiple cloning site.

The vectors used in this invention preferably have at least one "selection marker", which is a genetic element that allows the selection of genetically modified organisms/cells. These markers include antibiotic resistance genes such as, but not limited to ampicillin, chloramphenicol, tetracycline, kanamycin, hygromycin, bleomycin, phleomycin, puremycin and/or phenotype complementation genes, such as but not limited to methotrexate, dihydrofolate reductase, ampicillin, neomycin, mycophenolic acid, glutamine synthetase.

The term "expression vector" refers to any vector that is capable of transporting, transferring, and/or storing genetic material, and that once in the host cell, is used as a source of genetic information for the production of one or more gene products (gene expression).

In addition, the expression vectors of this invention may include one or more regulatory nucleotide sequences to control gene replication, transfer, transport, storage and expression of genetic material, such as origin of replication, selection marker, multiple cloning site, promoter (for example, T7 pol, pL and pR lambda phage, SV40, CMV, HSV tk, pgk, T4 pol, or EF-1 alpha and its derivatives), ribosome binding site, RNA splice site, site polyadenylation, signal peptide for secretion and gene transcription termination sequence. However, the vectors of expression of this invention are not limited thereby. The technique of incorporating the control sequences into a vector is well characterized in the state of the art.

The vector of expression used in this invention may also have "enhancer" sequences, also called "cis" elements which can influence positively or negatively the promoter-dependent gene expression.

A "coding sequence" refers to a nucleotide sequence that is transcribed into mRNA (messenger RNA) and translated into a polypeptide when under the control of appropriate regulatory sequences. The limits of the encoding sequence are determined by a translation initiation codon at the 5'-end of the DNA sense tape and by a translation termination codon at the 3' end of the DNA sense tape. As a result of genetic code degeneration, different DNA sequences can encode the same polypeptide sequence. Therefore, such degenerated substitutions in the coding region are considered to be inserted in the sequences described in this invention.

The term "promoter" is a minimum sequence of DNA sufficient to direct the gene transcription, i.e., a sequence that directs the binding of the RNA polymerase enzyme thus promoting messenger RNA synthesis. Promoters can be specific to the cell type, type of tissue and species, and in certain cases are modulated by regulatory elements in response to some external physical or chemical agent called inductor.

The terms "transformation" and "transfection" refer to the act of inserting a vector or other carrier vehicle of exogenous genetic material into a host cell, prokaryotic or eukaryotic, for transport, transfer, storage and/or genetic expression of genetic material of interest.

The term "recombinant expression" refers to the expression of recombinant polypeptide in host cells.

The term "host cell" refers to the cell that will receive the genetic material through a vector and/or cells that have already received the genetic material through a vector (transformed cells or transfected). These host cells can be either of prokaryotic (prokaryotic microorganisms) or eukaryotic (eukaryotic cells or microorganisms) origin.

In this application, the terms 'peptide', 'polypeptide' or 'protein' may be used interchangeably, and refer to an amino acid polymer connected by peptidic bonds, regardless of the number of amino acid residues that make up this chain. Polypeptides, as used here, include "variants" or "derivatives" of them, which refer to a polypeptide that includes variations or modifications, e.g. substitution, deletion, addition, or chemical modification in its amino acid sequence in relation to the reference polypeptide, provided the derived polypeptide has immunosuppressive activity, stability, midlife, pharmacokinetic characteristics, and/or physico-chemical characteristics equal or higher than initially observed for the original polypeptide. Examples of chemical modifications are glycosylation, PEGlation, PEG alkylation, alkylation, phosphorylation, acetylation, amidation, etc. The amino acids in the polypeptides of the invention, depending on the orientation of the amino group of the carbon alpha atom may belong to the L series or D. Polypeptide may be artificially produced from cloned nucleotide sequences using the recombinant DNA technique ("recombinant polypeptide") or can be prepared by a known chemical synthesis reaction ("synthetic polypeptide").

The term "amino acid substitutions" refers to the substitution of at least one polypeptide amino acid residue for the production of derivatives with asparaginase activity, stability, midlife, pharmacokinetic characteristics, and/or physico-chemical characteristics equal to or better than those initially observed for the original polypeptides. Replacement amino acids can be natural, modified, or unusual.

In this respect, the term 'conservative replacement of amino acids' refers to the replacement of amino acids in a polypeptide by those with similar side chains and, therefore, with remarkably close physical and chemical properties. For example, exchanging an alanine for a valine or leucine or isoleucine is considered conservative, since the amino acids involved have as a common characteristic an aliphatic lateral chain. The group containing as a characteristic a basic side chain is composed of lysine, arginine and histidine. The group containing sulfur in the lateral chain comprises the amino acids cysteine and methionine. The amino acids phenylalanine, tyrosine and tryptophan contain an aromatic side chain. Asparagine and glutamine are part of the side-chain amino acids containing amide, while serine and threonine contain a hydroxyl bound to their aliphatic sidechain. Other examples of conservative replacement include replacement of an apolar amino acid or hydrophobic like isoleucine, valine, leucine, or methionine for another, also apolar. Similarly, the invention described here contemplates the substitution of polar amino acids or hydrophilics such as arginine per lysine, glutamine per asparagine and threonine per serine. Additionally, substitution between basic amino acids such as lysine, arginine or histidine or the substitution between amino acids of acid character such as aspartic acid or glutamic acid is also contemplated. Examples of conservative replacement of amino acids are: valine by leucine or isoleucine, phenylalanine by tyrosine, lysine by arginine, alanine by valine and asparagine by glutamine.

In addition, illustrative examples of modified or unusual amino acids include 2-Aminoadipic acid, 3-Aminoadipic acid, beta-alanine, 2-Aminobutyric acid, 4-aminobutyric acid, 6-aminocaproic acid, 2aminoheptanic acid, 2aminoisobutyric acid, 3aminoisobutyric acid, 2aminoheptanic acid, 2aminopimelic acid, 2,4-diaminobutyric, desmosin, 2,2'-diaminopimelic acid, 2,3-diaminopropionic acid, N-ethylglycine, N-ethylasparagine, hydroxylisin, alohydroxylisin, 3-hydroxyproline, 4-hydroxyproline, isodesmosin, aloisoleucine, N-methyl glycine, N-methyl isoleucine, 6-N-methyllysine, N-methyl valine, norvaline, norleucine, ornithine, etc.

The objects of this invention will be better understood from the detailed description of the invention and the attached claims.

DETAILED DESCRIPTION OF THE INVENTION

Unless they are defined differently, all the technical and scientific terms used here have the same meaning understood by a technician on the subject to which the invention belongs. The terminology used in the description of the invention is intended to describe particular achievements only, and has no intention of limiting the scope of the teachings. Unless otherwise stated, all figures expressing quantities, percentages and proportions, and other numerical values used in the specification and the claims should be understood as being modified in all cases by the term "approximately". Thus, unless otherwise stated, the numerical parameters shown in the specification and the claims are approximations that may vary, depending on the properties to be obtained.

The present inventors solved the problem of the state of the art by providing polypeptides with asparaginase activity by modifying human L-asparaginase (SEQ ID NO:1), having in its sequence a proton acceptor in the position occupied by free glycine in the wild protein and, consequently, with an improved self-processing mechanism.

The auto cleavage mechanism starts with a proton acceptor solution from the T168 hydroxyl group. After deprotonation, T168 (with increased nucleophilic character) attacks the carbonyl group of G167 forming a covalent bond that will be hydrolyzed. The complete cleavage between the two residues leaves the amino grouping of T168 free to catalyze the hydrolysis of asparagine.

It is observed that the essential residue T168 of ASRGL1 plays a double role: first, its lateral chain is necessary for the autocleavage reaction and second, with the rupture of the peptide bond between G167 and T168, the T168-free amino group participates in the catalysis of asparagine hydrolysis.

In inactive protein, the distance between T168 hydroxyl and G167 carbonyl is 4.0 Å, which does not favor the chemical events necessary for self-processing, showing the need for a conformational shift to cleavage. The self-processing causes a relaxation in the T168 lateral chain, bringing the T168 hydroxyl closer to the active site, since the distance between this hydroxyl and the amino group of T168 is reasonable 2.7 Å.

The proximity of glycine to the T168 hydroxyl grouping provides its operation as an extrinsic self-processing primer. An intrinsic initiator would be advantageous for activating this process since the translation of the protein. In this context, the inventors of the present invention introduced a proton acceptor in the position occupied by free glycine and thus improved the in vitro self-processing mechanism.

Although free glycine acts satisfactorily as a proton acceptor, the same is not true for glycine included in a protein structure. In a protein, its amino and carboxyl groups form the peptide bond and are not free to act in the sense of protons. Moreover, its lateral chain formed only by hydrogen does not perform this function.

Since blood pH is 7.4, glutamic acid, aspartic acid and histidine could act as a proton acceptor in the blood. These amino acids have in common the pKa of the lateral chain lower than blood pH, so under these conditions there is a predominance of COO— radicals over COOH.

The conformational change in the auto cleavage region can be facilitated by glycine 9 (G9). G9 is part of a glycine rich loop called the HGG loop (Histidine 8-Glycine 9-Glycine 10). This loop is strongly conserved (~100%) throughout the phylogeny of L-asparaginases plant-type.

In the inactive protein structure, the position of G10 carbonyl favors hydrogen binding between Gil and T219 and blocks the HGG loop in a closed conformation. In addition, the close proximity (1.6 Å) between G9 of the HGG and L166 loop contributes to the closed conformation. In contrast, in the active enzyme, the rotation of G9 modifies the position of the G10 carbonyl resulting in the position change of the HGG loop.

Given the flexibility of the HGG loop and its importance for activating self-processing, this region was considered for mutation purposes aimed at improvement of the self-processing mechanism.

Through in silico modifications to ASRGL1 structures the inventors observed that a mutation in G10 to an amino acid working as a proton acceptor could place the carboxyl of the lateral chain near the active site, in a position similar to free glycine which optimizes the self-processing reaction.

The studies showed that the mutated protein had a higher proportion of auto-processing compared to the wild protein. The proposed changes in the present invention have been able to raise the rates of self-processing and of human L-asparaginase enzyme activity, achieving the goal of improving autocleavage and hydrolysis reactions, as demonstrated by the examples presented here.

In a first aspect, the present invention provides a polypeptide with selected asparaginase activity from the group consisting of:
(i) a polypeptide that has an increased rate of auto-processing compared to human L-asparaginase in the wild presented in SEQ ID NO: 1;
(ii) a polypeptide comprising the amino acid sequence having at least 90% identity with the sequences of any of the SEQ ID NOs: 3-5;
(iii) a polypeptide in which the amino acid glycine at position 10 of the SEQ ID NO: 1 is replaced by an amino acid selected from the group consisting of glutamic acid, aspartic acid and histidine;
(iv) a polypeptide comprising the amino acid sequence presented in any of the SEQ ID NO: 3-5; e
(v) a polypeptide of (i) to (iv) comprising one or more conservative amino acid substitutions.

In one respect, the polypeptides of this invention are at least 90%, at least 91%, at least 92%, at least 93%, at least 94%, at least 95%, at least 96%, at least 97%, at least 98% or at least 99% identical to the SEQ ID NOs amino acid sequences: 3-5.

In an embodiment, the polypeptide of invention comprises the amino acid sequence of any of the SEQ ID NO:3-5, where the amino acid glycine at position 10 of SEQ ID NO: 1 is replaced by glutamic acid, aspartic acid and histidine respectively.

In a preferred embodiment, the polypeptide of invention comprises the amino acid sequence of SEQ ID NO:3, where the amino acid glycine in heading 10 of SEQ ID NO: 1 is replaced by glutamic acid (G10E mutation).

The induction of the recombinant expression of ASRGL1 (SEQ ID NO: 1) and ASRGL1_G10E (SEQ ID NO: 3) in *E. coli* allowed the production of a greater amount of protein for self-processing analysis. A band of ~38 kDa, indicated in FIG. 1 corresponds to the unprocessed protein and the band of ~24 kDa corresponds to the chain a. The 13 chain is not visualized, as the histidine tail is in the N-terminal portion of the protein. Besides the 38 kDa and 24 kDa bands, a third band of ~45 kDa was observed.

Figure 2:
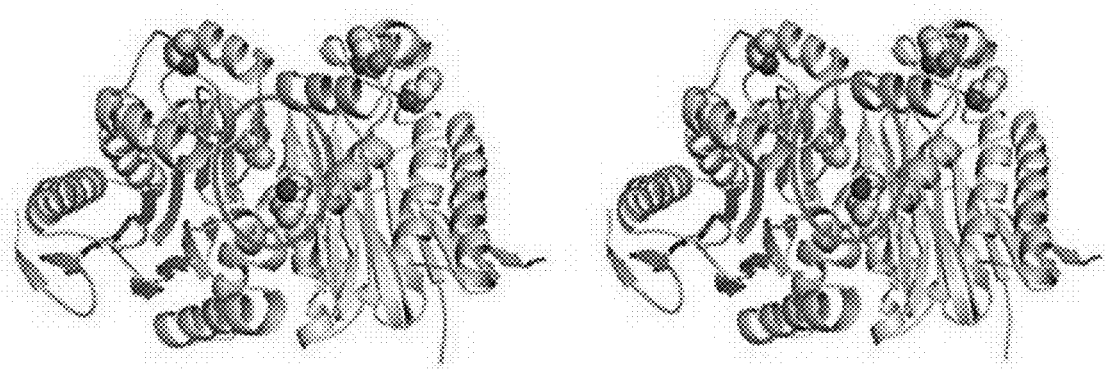
FIG. 2 shows a structural analysis and electrophoretic profile of ASRGL1 dimers in different cleavage states.
Figure 2:
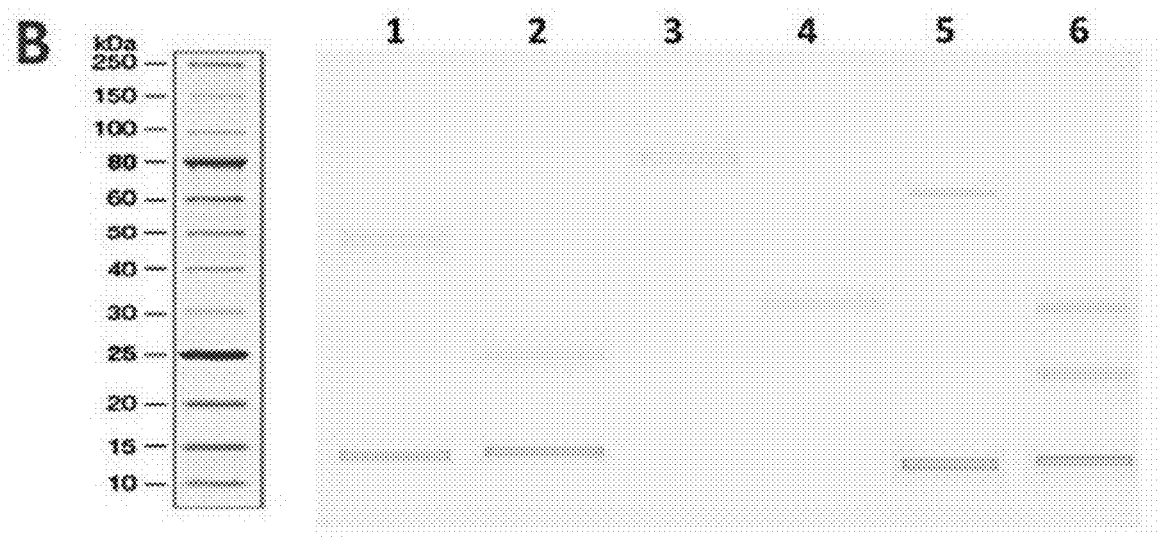

The ~45 kDa band is believed to correspond to a chain dimer a connected by a disulphide bridge (SS bridge). This is based on the state of the art reports (Li et al. (2016)), in its size corresponding to twice the size of the chain a and also based on the existence of three cysteines in this chain that could form disulphide bridges (FIG. 2a). It is known that because it is a strong covalent bond, the reducing agents of the electrophoresis sample buffer are often not efficient enough in breaking this strong interaction and so you can see a band on the gel corresponding to dimers with disulphide bridge. If this dimerized fraction were not processed we would have a band of approximately 75 kDa, however, as only a migration of 45 kDa can be seen, it is concluded that this is the processed state with disulphide bridge (FIG. 2b).

In FIG. 2a, the cartoon representation of processed and unprocessed ASRGL1 dimers. Chain α in beige, chain β in green, cysteines in colored spheres according to the atom where C—gray, N—blue, O—red and S—yellow. The oval circle in red describes the most likely region of disulphide bridge formation between the monomers.

FIG. 2b shows the theoretical electrophoretic profile of dimers in different processing situations, where: 1—dimers connected by a disulphide bond composed of two cleaved monomers (45 kDa band—chain a with SS bridge, 15 kDa band—chain β), 2—dimers not connected by disulphide link composed of two cleaved monomers (24 kDa band—chain α, 15 kDa band—β chain), 3—dimers connected by disulphide bond composed of two unbonded monomers (75 kDa band corresponding to 38 kDa continuous protein connected by disulphide bridge), 4—inactive dimerized sample without disulphide bridge (35 kDa band corresponding to continuous polypeptide chain), 5—dimer connected by partially cleaved disulphide bond (only one monomer is cleaved, 65 kDa band corresponding to two chains α and one β and 15 kDa band corresponding to chain β), 6—dimers not connected by a partially cleaved disulphide link (only one monomer is cleaved, 38 kDa band corresponding to unglued protein, 24 kDa band corresponding to chain α and 15 kDa band corresponding to chain β of the cleaved monomer).

From the analysis of the content of each state, it was concluded that the mutated protein showed a higher proportion of auto-processing compared to the wild protein. In addition, the G10E mutation favored the formation of the 45 kDa intermediary.

The fractions of ASRGL1 (SEQ ID NO: 1) and ASRGL1_G10E (SEQ ID NO: 3) presented different kcat values, as it was already expected since different states of intramolecular self-processing were found.

Considering that kcat is the maximum number of mols of substrate that can be converted into a product per mole of enzyme in a given unit of time, it was observed that ASRGL1_active showed the highest enzymatic efficiency among the three states of wild asparaginase, aSRGL1_intiva_a and ASRGL1_intiva_b had similar kcat values (see Example 5).

The mutation proposed by this invention is the first modification of ASRGL1 capable of increasing the rates of both self-processing and enzymatic activity. The two fractions of ASRGL1_G10E had the highest kcat values. A replacement G9A presented kcat 0.0126 s-1 and G10A kcat 0.0053 s-1.

The G10E mutation achieved the objective of improving in vitro autocleavage and hydrolysis reactions on asparagine, but further studies are still necessary in order to completely clarify the mechanism by which this mutation promoted such an effect.

In one embodiment, the polypeptide of invention is for use in cancer prevention or treatment. In a preferred embodiment, cancer is selected from acute myeloid leukemia (ALL) chronic lymphoid leukemia, ovarian cancer, brain cancer, prostate cancer, pulmonary adenocarcinoma, non-Hodgkin's lymphoma and sarcoma (lymphosarcoma, reticulosarcoma and melanosarcoma). In a more preferred embodiment, cancer is acute myeloid leukemia (AMI).

In a second aspect, the present invention provides polynucleotides that encode the polypeptides described here.

Polynucleotides according to the invention comprise the nucleic acid sequences of any of the SEQ ID NO: 6-8 and their degenerations.

A technician in the field would recognize that degenerations are fully supported on the basis of the information provided in the application and the common knowledge of the state of the art. For example, the degeneration of the genetic code (i.e. different codons can encode the same amino acids) is a common knowledge in the technique and the identity of the amino acid encoded by each codon is well established.

On the basis of the information well known and established in the state of the art, the technician in the subject is able to identify nucleotide substitutions that do not alter the resulting amino acid sequence. For example, if a nucleotide sequence contains the CTA codon that encodes for a leucine, a technician in the field would understand that replacing the "A" with any other nucleotide (i.e, T, C or G) would still result in a codon coding for leucine. Thus, when in possession of both the nucleotide sequence of a gene and the amino acid sequence of the encoded protein, the technician in the subject will easily identify the degenerations that encode the same protein, with the same sequence of amino acids.

The use of the preferred codons can be adapted according to the host cell in which the nucleic acid is to be transcribed. These steps can be carried out according to methods well known to the versed in the technique and of which some are described in the reference manual Sambrook et al. (Sambrook et al, 2001).

In this sense, different species can display a preferential "codon usage". See Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opinion. Genet. Dev.* 4:851 (1994), Kane, *Curr. Opinion. Biotechnol.* 6:494 (1995), and Makrides, *Microbiol. Rev.* 60:512 (1996). As used here, the term "códon usage preferencial", or "preferential codons" is a term used in the art referring to codons that are most often used in cells of certain species. For example, the amino acid threonine (Thr) can be encoded by ACA, ACC, ACG, or ACT, but in mammalian cells, ACC is the most commonly used codon. In other species, for example, different Thr codons may be preferred. Preferred codons for a particular species can be introduced into the polynucleotides of this invention by a variety of methods known in the art. The introduction of preferential codon sequences into a recombinant DNA can, for example, to increase polypeptide production by making translation more efficient in a given cell type. Thus, the polynucleotide sequences of the invention can be optimized for different species.

The polynucleotides of this invention are obtained by methods already known in the state of the art, such as those described by Sambrook et al. (2001). For example, additional sequences can be identified and functionally noted by comparing sequences. Therefore, a technician in the field can readily identify a sequence functionally equivalent to the polynucleotides of the present invention in a suitable database as, for example, GenBank, using publicly available sequence and parameter analysis programs.

In another example, polynucleotides from the invention can be obtained through a reverse transcription reaction followed by PCR amplification. Both oligo-dT and randomic initiators can be used in the reverse transcription reaction to prepare single tape cDNAs, from the isolated RNA of the *L. muta* snake, which contain the sequences of interest. RNA can be isolated by methods known as the use of Trizol reagent (GIBCO-BRL/Life Technologies), Gaithersburg, Maryland).

Gobinda et al. (PCR Methods Applic. 2:318-22, 1993), describes "restriction-site PCR" as a direct method using universal primers to obtain unknown sequences adjacent to a known locus. First, the genomic DNA is amplified in the presence of an adaptor-initiator, which is homologous to an adaptor sequence attached to the ends of the genomic DNA fragments, and in the presence of a specific initiator for a known region. The amplified sequences undergo a second round of PCR with the same adapter-initiator and another specific initiator, internal to the first. Products from each PCR round are transcribed with a suitable RNA polymerase and sequenced using a reverse transcriptase.

Still in an illustrative way, the inverse PCR allows the obtaining of unknown sequences starting with primers based on a known region (Triglia, T. et al., Nucleic Acids Res 16:8186, 1988). The method uses several restriction enzymes to generate a fragment in the known region of the gene. The fragment is then circularized by intramolecular connection and used as a mold for PCR. Divergent initiators are drawn from the known region.

In addition, it is known that sequences with reduced degrees of identity can also be obtained with the aid of degenerate primers and PCR-based methodologies.

Typically, the nucleic acid sequence of a primer useful for amplifying nucleic acid molecules by PCR can be based on the amino acid sequences of the polypeptides of the invention represented, for example, by the SEQ ID NOs: 3 a 5. In this invention, the initiating oligonucleotides used for the amplifications of genes coding for human wild L-asparaginase (ASRGL1) and mutated human L-asparaginase (ASRGL1_G10E; SEQ ID NO: 3) are represented by SEQ ID NOs: 9-11.

In a third aspect, the present invention provides an expression cassette comprising a polynucleotide according to the invention operationally linked to the sequences necessary for its expression. Typically, coding and regulatory regions are heterologous with each other.

In a fourth aspect of this invention, this invention provides an expression vector comprising a polynucleotide or an expression cassette according to the invention. This expression vector can be used to transform a host cell and allow the expression of nucleic acid according to the invention in the cell.

With advantage, the expression vector comprises regulatory elements that allow the expression of nucleic acid and elements that allow its selection in the host cell according to the invention. The methods for selecting these elements according to the host cell in which the expression is desired, are well known of the versed in the technique and widely described in literature.

Vectors can be constructed by classical molecular biology techniques, well known from the versed in the technique. Non-limiting examples of expression vectors suitable for expression in host cells are plasmids and viral or bacterial vectors.

In a fifth aspect of this invention, this invention provides a polynucleotide, expression cassette or expression vector according to the invention to transform or transfect a cell. The host cell may be transformed/transferred in a transient or stable manner and the nucleic acid, cassette or vector may be contained in the cell in the form of an episome or in chromosomal form.

The polynucleotide, expression cassette or vector is inserted into competent prokaryotic or eukaryotic host cells. The recombinant clones are selected and then submitted to analysis by restriction enzymes and DNA sequencing, allowing the confirmation of the cloned sequence, using methods, kits and equipment widely known by a technician on the subject.

Thus, the polypeptides of invention can be prepared using recombinant DNA technology, in which a cassette or expression vector comprising a polynucleotide sequence of invention, for example, which encodes any of the SEQ ID Nos polypeptides: 3 to 5, is operationally linked to a promoter. The host cells are cultivated under appropriate conditions and the polypeptide is expressed. The host cell can be a cell of bacteria, fungus, plant or animal The polypeptide is recovered from the culture, where the recovery may include a purification step of the polypeptide. The recombinant polypeptide obtained is analyzed and treated in order to solubilize it, when appropriate. The solubilized polypeptide is then purified and biochemically characterized using, for example, methods common to the field of biochemistry, such as HPLC, SDS-PAGE, Western Blotting, isoelectric focusing with pH gradient, circular dichroism. Using these methods, you can determine characteristics such as the yield of recombinant polypeptide expression; the determination of the characteristics of secondary structures, in addition to other characteristics whose determination is important for the development of a biotechnological drug.

Polypeptides can be expressed "fused" to a label. The term "tag" or the English term "tag" refers to embedded encoding sequences near the multiple cloning site of an expression vector, enabling its translation concomitant and adjacent to the sequence of the cloned recombinant polypeptide. Thus, the label is expressed fused to the recombinant polypeptide. Such labels are well known in the state of the art and include compounds and peptides such as polyhistidine, polyarginine, FLAG, glutathione S-transferase, maltose binding protein (MBP), cellulose binding domain (CBD), Beta-Gal, OMNI, thioredoxine, NusA, mistine, chitin-binding domain, cutinase, fluorescent compounds (such as GFP, YFP, FITC, rhodamine, lanthanides), enzymes (such as peroxidase, luciferase, alkaline phosphatase), chemiluminescent compounds, biotinyl groups, epitopes recognised by antibodies such as leucine zipper, c-myc, metal-binding domains and binding sites for secondary antibodies.

Polypeptides can also be obtained synthetically using methods known in art. Direct synthesis of the polypeptides of the invention can be performed using solid phase synthesis, synthesis in solution or other conventional media, usually using α-amino group, α-carboxyl and/or amino acid side chain functional groups. For example, in solid phase synthesis, an adequately protected amino acid residue is bound through its carboxyl group to an insoluble polymeric carrier, such as a polystyrene or polyamide cross-linked resin. Solid phase synthesis methods include both BOC and FMOC methods, which use tert-butyl carbonyl, and 9-fluorenylmethyloxycarbonyl as protective groups α-amino, respectively, both well known by technicians on the subject (Sambrook et al., Molecular Cloning: A Laboratory Manual, 2nd edition, Cold Spring Harbor Press, Cold Spring Harbor, N.Y; Ausubel et al., Current Protocols in Molecular Biology, John Wiley and Sons, New York, 1995).

The following protective groups may be examples used for the synthesis of polypeptides of invention: 9-fluorenylmethyloxycarboyl (Fmoc), tert-butylloxycarbonyl (Boc), carbobenzyloxy (Cbz), 2-chloro-3-indenylmethoxycarbonyl (Climoc), benz(f)inden-3-yl-methoxycarbonyl (Bimoc), 1,1-dioxobenzo[b]thiophene-2-yl-methoxycarbonyl (Bsmoc), 2,2,2-Trichloroethoxycarbonyl (Troc), 2-(trimethylsilyl)ethoxycarbonyl (Teoc), homobenzyloxycarbonyl (hZ), 1,1-dimethyl-2,2,2-trichloroethoxycarbonyl (TCBoc), 1-methyl-1 (4-biphenyl)ethoxycarbonyl (Bpoc), 1-(3,5-di-t-butylphenyl)-1-methylethoxycarbonyl (t-Bumeoc), 2-(2'- or 4'-pyridyl)ethoxycarbonyl (Pyoc), vinyloxycarbonyl (Voc), 1-isopropylaliloxycarbonyl (Ipaoc), 3-(pyridyl)allyl-oxycarbonyl (Paloc), p-methoxybenzyloxycarbonyl (Moz), p-nitrocarbamate (PNZ), 4-azidobenzyloxycarbonyl (AZBZ), Benzil (Bn) MeO, BnO, Metoxymethyl (Mom), methylthiomethyl (MTM), phenyldimethylsillmethoxymethyl (SMOM), t-butyldimethylsilyl (TBDMS), benzyloxymethyl (BOM), p-methoxybenzyloxymethyl (PMBM), nitrobenzyloxymethyl (NBOM), p-anisyloxylmethyl (p-AOM), pBuOCH20-, 4-pentenyloxymethyl (POM), 2-methoxyethoxymethyl (MEM), 2-(trimethylsilyl)ethoxymethyl (SEM), menthoxymethyl (MM), tetrahydropyranil (THP), —OCOCOph, Acetyl, ClCH2CO2-, —CO2CH2CCl3, 2-(trimethylsilyl)ethyl (TMSE), 2(p-toluenesulfonyl)ethyl (Tse). (Greene T. W. Wuts P. G. M., Protective groups in organic synthesis, 3rd ed., John Wiley & Sons, INC, New York, USA, 1999).

After the chemical reaction, the polypeptides can be separated and purified by a known purification method. An example of such purification methods may include a combination of solvent extraction, distillation, column chromatography, liquid chromatography, recrystallization and the like.

In a sixth aspect, a pharmaceutical composition is provided here comprising a polypeptide with asparaginase activity according to invention and at least one carrier or a pharmaceutically acceptable excipient.

Pharmaceutically acceptable carriers or excipients are selected according to the final presentation of the composition of the present invention, which can be in the form of capsules, tablets or solution for oral administration, solution for nasal administration, solution for injection for intramuscular, intravenous, cutaneous or subcutaneous.

Pharmaceutically acceptable excipients, carriers or stabilizers are not toxic to the recipient organism in the dosages and concentrations employed and include buffers such as phosphate, citrate and other organic acids; antioxidants such as ascorbic acid and methionine; preservatives such as octadecyl dimethyl benzyl ammonium chloride, hexamethonium chloride, benzalkonium chloride, benzethonium chloride, phenol, butyl alcohol, benzyl alcohol, alkyl parabens such as methyl and propyl paraben, catechol, resorcinol, cyclohexanol, 3-pentanol and m-cresol; proteins such as albumin, gelatin or immunoglobulins; amino acids, monosaccharides, disaccharides and other carbohydrates such as glucose, mannose, sucrose, mannitol or sorbitol; polymeric excipients such as polyvinylpyrrolidones, Ficoll®, dextrins and polyethylene glycols; flavoring agents; sweeteners; antistatic agents; chelating agents such as EDTA or EGTA; ion releasing salts such as sodium; metal complexes; non-ionic surfactants such as polysorbates 20 and 80; lipids such as phospholipids, fatty acids and steroids such as cholesterol. Methods for preparing various pharmaceutical compositions are well known, or will be apparent in the light of this invention, by the art expert in pharmaceutical technology.

In addition, the compositions may include additives in order to increase ease of administration, storage capacity and resistance to degradation, bioavailability, half-life, providing isotonic preparations, etc. Additives used for the preparation of pharmaceutical compositions are well known in the art.

In an embodiment, the composition according to the present invention comprises at least one additional chemotherapeutic agent selected from among alkylating agents, antimetabolites, kinase inhibitors, anti-spindle poison plant alkaloids, cytotoxic/antitumor antibiotics, topoisomerase inhibitors, photosensitizers, antiestrogens and selective estrogen receptor modulators (SERMs), antiprogesterones, estrogen receptor descending regulators (ERDs), estrogen receptor antagonists, luteinizing hormone release agonists, antiandrogens, aromatase inhibitors, EGFR inhibitors, inhibitors of VEGF, antisense oligonucleotides that inhibit the expression of genes involved in abnormal cell proliferation or tumor growth. Chemotherapeutic agents useful in the treatment methods of this invention include cytostatic and/or cytotoxic agents.

The pharmaceutical compositions of this invention must comprise a therapeutically effective quantity of the polypeptide. For any compound, the therapeutically effective dose can be estimated initially, either in cell culture trials, e.g. of neoplastic cells, or in animal models, usually mice, rabbits, dogs or pigs. The animal model can also be used to determine the appropriate concentration range and the route of administration. Information of this kind can then be used to determine usable doses and routes of administration in humans.

The pharmaceutical composition according to the present invention comprises from 0.1% to 99% w/w, preferably 1% to 60% w/w, particularly 10% to 50% w/w of the polypeptides of the present invention.

According to the present invention, the administration of the said pharmaceutical compositions can be done by oral, sublingual, nasal, intravenous, intramuscular, intraperitoneal, intra-articular, subcutaneous, cutaneous, transdermal routes of administration and is not limited to these. In a preferred embodiment, the composition of the present invention is for intravenous administration.

In a seventh aspect, this invention provides the use of the invention's polypeptides in the manufacture of a medicine for cancer prevention or treatment. In a preferred embodiment, cancer is selected from acute myeloid leukemia (AMI), chronic lymphoid leukemia, ovarian cancer, brain cancer, prostate cancer, lung adenocarcinoma, non-Hodgkin's lymphoma and sarcoma. In an embodiment, sarcoma is selected from lymphosarcoma, reticulosarcoma and melanosarcoma. In a preferred embodiment, cancer is acute myeloid leukemia (ALL).

This invention also refers to a method for producing polypeptide according to the invention with asparaginase activity comprising the insertion of a polynucleotide, a cassette or an expression vector according to the invention in an in vivo expression system and the collection of the polypeptide produced by that system. Numerous in vivo expression systems, including the use of appropriate host cells, are available in the trade and the use of these systems is well known for its technical expertise.

Particularly suitable expression systems include microorganisms, such as bacteria transformed with bacteriophage, plasmid or cosmid recombinant DNA expression vectors; yeast transformed with yeast expression vectors; insect cell systems infected with virus expression vectors (eg, baculovirus); plant cell systems transformed with virus expression vectors (for example, cauliflower mosaic virus, CaMV \; tobacco mosaic virus, TMV \) or with vectors of bacterial expression (for example, Ti or pBR322 plasmids); or animal cell systems. It is also possible to employ cell-free translation systems to produce the polypeptides of invention.

The introduction of polynucleotides that encode a polypeptide of this invention into host cells can be performed using methods described in many standard laboratory manuals, as Davis et al., Basic Methods in Molecular Biology (1986) and Sambrook et al., Molecular Cloning: Laboratory Manual, Cold Spring Harbor, N.Y. (1989).

The transformed or transfected host cell described above is then grown into a suitable nutrient medium under conditions conducive to the expression of the invention's immunosuppressive polypeptides. The medium used to grow the cells can be any conventional medium suitable for developing the host cells, as a minimum or complex medium containing appropriate supplements. The appropriate means are available from commercial suppliers or can be prepared according to published recipes (for example, in the American Type Culture Collection catalogues). The polypeptides of the invention produced by the cells can then be recovered from the cell or culture medium by conventional procedures including separating the host cells from the medium by centrifugation or filtration, precipitating the aqueous protein components of the supernatant or filtered by means of a salt, e.g. ammonium sulphate, purification by a variety of chromatographic procedures, e.g. ion exchange chromatography, exclusion chromatography, hydrophobic interaction chromatography, gel-filtration chromatography, affinity chromatography or depending on the type of polypeptide in question.

According to an eighth aspect of the invention is provided a method to produce a polypeptide with asparaginase activity according to the invention comprising:
  (a) transfer to a host cell a polynucleotide of the present invention to obtain a transformed or transfected host cell;
  (b) grow the transformed or transfected host cell to obtain a cell culture;
  (c) express the polynucleotide of the present invention in a host cell transformed or transfected to produce a polypeptide; and
  (e) isolate the polypeptide from the present invention of the cell or cell culture.

In one particular aspect of the invention, the host cell is a prokaryotic microorganism or a eukaryotic cell or microorganism. In an additional aspect of the invention, said polypeptide is provided with a "tag".

In a ninth aspect of the invention, a method of cancer prevention or treatment is provided, characterized by understanding the administration to an individual in need of such prevention or treatment of a therapeutically effective amount of a polypeptide according to the invention.

The actual amount needed for a human individual will depend on the severity of the individual's disease state, general health, age, weight, and gender, and diet, the time and frequency of administration, drug combination/combinations, reaction sensitivities, and tolerance/response to therapy. Thus, doses to be provided depend on a number of factors that cannot be measured before clinical trials are conducted. The technician on the subject, however, knows how to arrive at suitable doses for different treatments.

The following examples are merely illustrative and should only be used for a better understanding of the developments in the present invention, should not, however, be used in order to limit the objects described.

EXAMPLES

Example 1

Cloning

The synthetic gene for ASRGL1 was designed with restriction sites for the enzymes NdeI and XhoI using the sequence deposited on GenBank (GI:20799289). GenScript (New Jersey, United States) performed gene synthesis and cloning in the pUC57 vector (ASRGL1-pUC57).

1.1 Drawing of Oligonucleotides

The G10E mutation was inserted in the amplification step of the ASRG1 gene, since the target region is at the beginning of the sequence. The initiating oligonucleotides used for the amplifications of genes coding for human wild L-asparaginase (ASRGL1) and mutated human L-asparaginase (ASRGL1_G10E) are described in Table 1.

TABLE 1

Sequence of oligonucleotides used for the amplification of human wild L-asparaginases (ASRGL1) and mutated (ASRGL1_G10E) with their respective restriction sites.

| Oligonucleotide | Sequence (5' - 3') | Restriction Site | SEQ ID NO: |
| --- | --- | --- | --- |
| ASRGL1 Forward | CATATGAATCCCATCGTAGTGGTC | NdeI | SEQ ID NO: 9 |
| ASRGL1_G10E Forward | CATATGAATCCCATCGTAGTGGTCCACGGCGAAGGAGCC | NdeI | SEQ ID NO: 10 |
| ASRGL1 Reverse | CTCGAGTTAGGGAAGGTCGGTGATAGT | XhoI | SEQ ID NO: 11 |

Note:
The ASRGL1 Reverse initiator was used for the amplification of both wild and mutated constructions. The underlined codon in ASRGL1_G10E Forward initiator corresponds to the G10E mutation.

1.2 PCR Gene Amplification

The ASRGL1 and ASRGL1_G10E constructs were amplified by polymerase chain reaction (PCR) (MULLIS et al., 1986) from the synthetic gene ASRGL1-pUC57 to a total volume of 20 µL, using 6.75 ng DNA, 2 µL 10× PCR Buffer (Invitrogen), 1.6 µL 10 mM dNTPs (Invitrogen), 5 µM each pair oligonucleotide, 0.8 µL 50 mM MgCl2, 1 µL of Taq DNA Polymerase. The program was started at 94° C. for 5 minutes, followed by 30 cycles of: 94° C./30 s, 70° C./30 s, 72° C./60 s and finished at 72° C. for 15 minutes. The ring temperatures (X) used in each reaction are shown in Table 2.

TABLE 2

Ring temperatures for PCR reaction.

| Construction | Ring temperature (X ° C.) |
| --- | --- |
| ASRGL1 | 58.9 |
| ASRGL1_G10E | 86.7 |

1.3 Agarose Gel Electrophoresis

Figure 3:
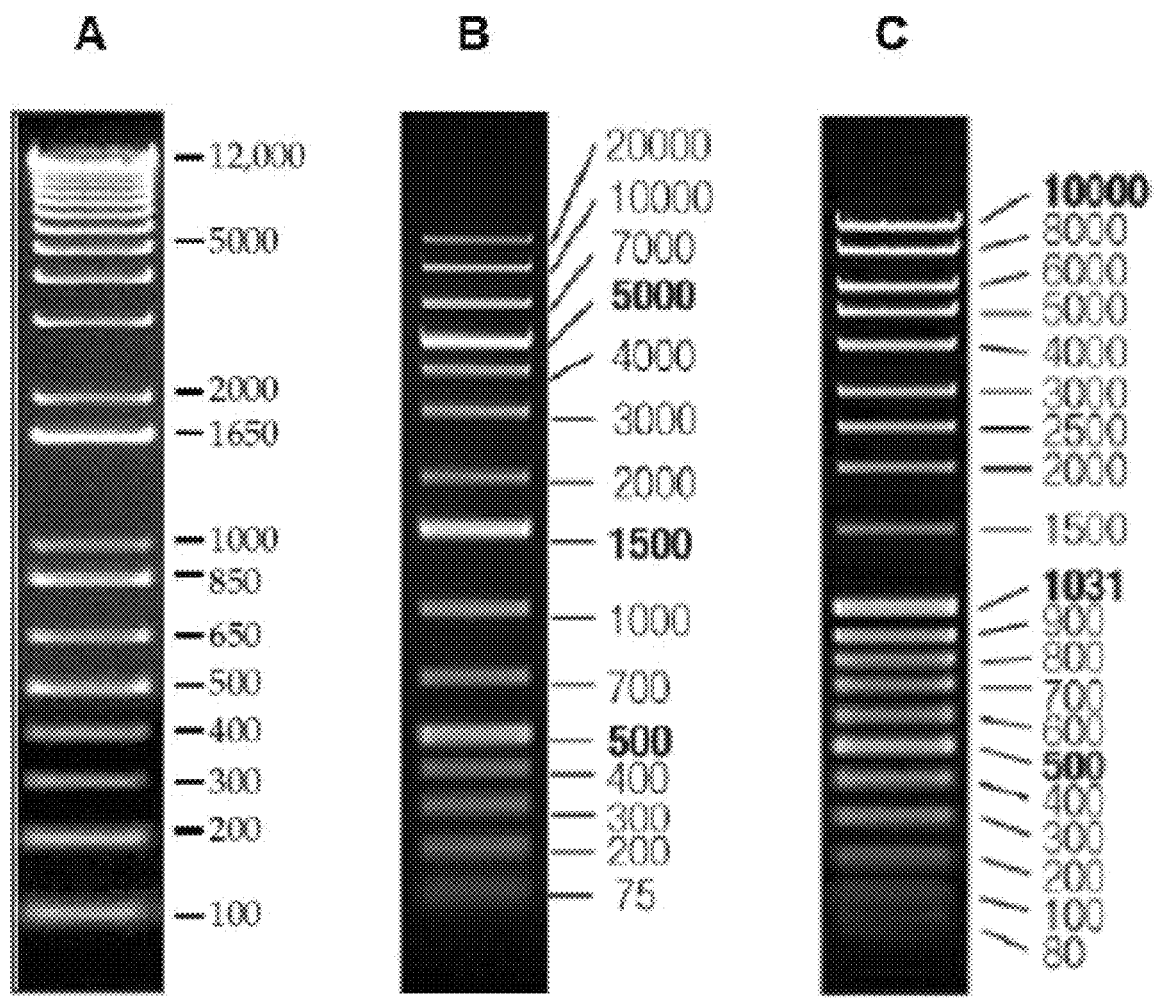
FIG. 3 shows the molecular weight patterns used for the agarose gel electrophoresis test.

DNA electrophoresis was performed on 1% agarose gel. 1 Kb Plus DNA Ladder (Invitrogen), O'GeneRuler 1 kb Plus DNA Ladder (Thermo Scientific) were used as molecular weight standard and MassRuler DNA Ladder Mix (Thermo Scientific). The electrophoresis was performed at 90 V for 1 hour. FIG. 3 shows these molecular weight standards, A) being the one shown, 1 Kb Plus DNA Ladder (Invitrogen); B) O'GeneRuler 1 kb Plus DNA Ladder (Thermo Scientific) and C) MassRuler DNA Ladder Mix (Thermo Scientific).

Figure 4:
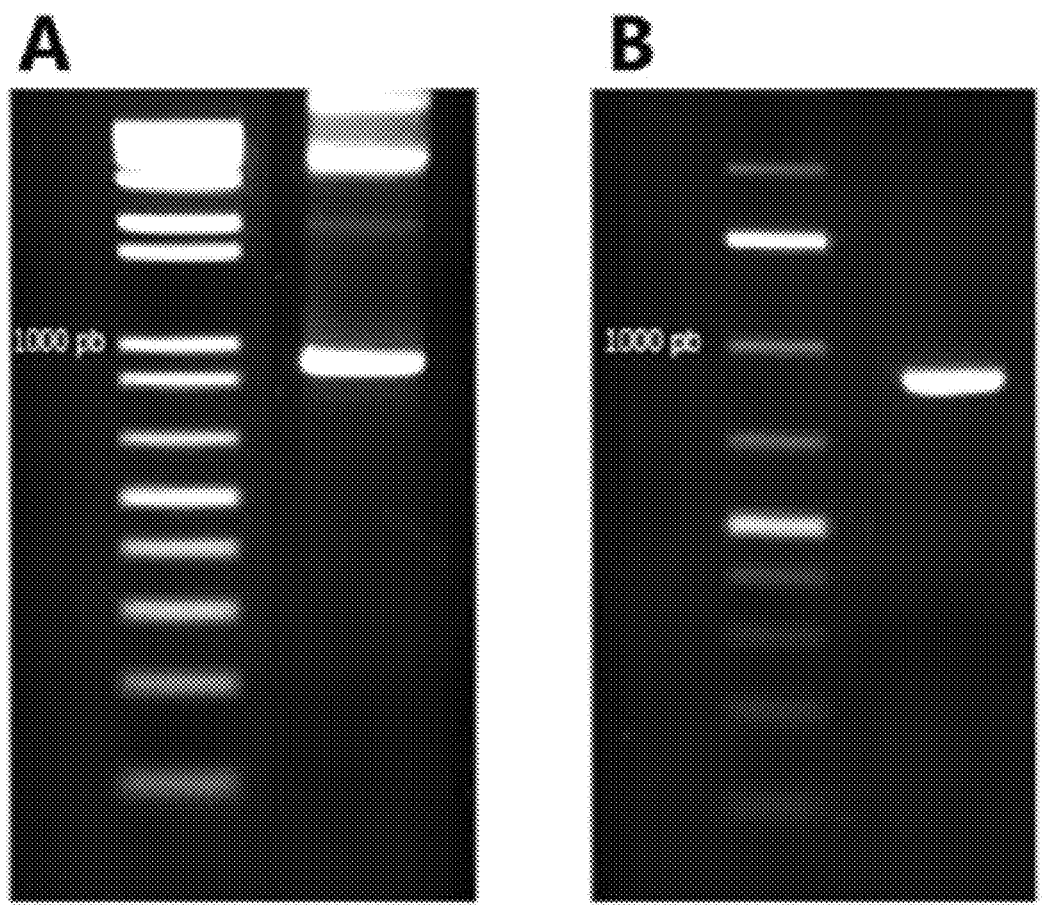
FIG. 4 shows the electrophoretic profile of the PCR products of ASRGL1 and ASRGL1_G10E sequences.

The amplification of the ASRGL1 and ASRGL1_G10E encoding sequence by PCR has amplified an approximate 950 bp size sequence that corresponds to the ASRGL1 gene size (944 bp). FIG. 4 shows the electrophoretic profile of the PCR products of ASRGL1 and ASRGL1_G10E sequences. In A, ASRGL1 (944 bp) (MW: 1 Kb Plus DNA Ladder, Invitrogen) and in B, ASRGL1_G10E (944 pb) (M: O'GeneRuler 1 kb Plus DNA Ladder, Thermo Scientific).

1.4 DNA Extraction from Agarose Gel

After agarose gel electrophoresis of the PCR products, the desired nucleotide sequence bands were excised and purified using low melt agarose electrophoresis. DNA was separated from agarose after incubation at 65° C. for 15 minutes and subsequent addition of phenol at room temperature.

1.5 Connection in Cloning Vector

The pGEM®-T Easy (Promega) vector insert was connected using 3 µL purified sample of the gel, 5 µL 2× Binding Plug (Promega), 1 µL of pGEM®-T Easy (Promega) and 1 µL of T4 DNA Ligase (Promega). Incubation was at 4° C. for 16 hours.

1.6 Preparation of Calcium-Competent Bacteria

For the preparation of calcium-competent bacteria, the CaCl2 method described by Sambrook et al. (2001). A colony of E. coli DH5α was inoculated with 5 mL of Luria-Bertani (LB) culture medium; 10.0 g/L of Bactotriptone; 5.0 g/L of NaCl and 5.0 g/L of yeast extract) containing appropriate antibiotic. The culture was incubated at 37° C. for 18 hours under constant agitation of 200 rpm. A volume of 1 mL of this crop was transferred to 250 mL of LB medium. The cells were incubated at 37° C. under the same stirring conditions until reaching the exponential growth phase (D.O.600 of 0.6).

The culture was centrifuged at 2,700×g for 10 minutes at 4° C. and the cells were suspended in 30 mL of Transformation Buffer I and kept on ice for 15 minutes. The suspension was centrifuged at 580×g for 15 minutes at 4° C., the cells were suspended in 10 mL of Processing Buffer II, kept in dry ice for 2 hours and then aliquoted and stored at −70° C.

1.7 Transformation of Calcium-Competent Bacteria

Recombination or binding reactions were incubated with 70 µL of the E. coli calcium-competent suspension for 30 minutes on ice. After this period, the cells were submitted to thermal shock through incubation at 42° C. for 2 minutes, followed by incubation for 2 minutes on ice and then adding 1 mL of LB medium for incubation under constant stirring of 200 rpm at 37° C. for one hour. Aliquots of 100 µL were distributed in half LB-agar (half LB with the addition of 1.5% agar-agar) added of antibiotic (selective medium) according to the resistance conferred by the vector used in the transformation of bacteria and incubated at 37° C. for 16 hours.

Particularly in the case of pGEM-T Easy cloning, LB-agar medium was added of 100 µg/mL ampicillin, 0.04 mg/mL X-gal (5-bromo-4-chloro-3-indoxyl-β-D-galactopiranoside) and 0.4 mM isopropyl-β-D-tiogalactopyranoside (IPTG) inductor. In this case, the selection of the positive clones was made by color analysis of the colonies due to the presence or absence of expression of the enzyme β-galactosidase. This, whose expression is induced by IPTG, degrades the X-gal substrate producing a blue substrate. If the fragment is incorporated into the vector, the enzyme β-galactosidase is not expressed and the colonies remain white, facilitating the identification of positive clones, which were later sequenced.

1.8 Small-Scale Plasmid DNA Extraction

The positive clones had their plasmid DNA extracted. For this purpose, a colony was selected and incubated in 5 mL of LB medium under stirring of 200 rpm at 37° C. for 16 hours. The bacterial cells were centrifuged and suspended at 250 µL of Buffer containing 50 mM glucose, 25 mM Tris HCl pH 8.0 and 10 mM EDTA pH 8.0. 250 µL of Buffer containing NaOH 0.2N, SDS 1% followed by agitation to rupture the cells has been added, and immediate addition of 3 M Potassium Acetate Buffer, 11.5% (v/v) Glacial Acetic Acid. After centrifugation to remove the cell remains, the fraction containing nucleic acid was separated by incubation with phenol: chloroform (1:1). Plasmids were precipitated by the addition of Ethanol and then suspended at 10 mM Tris-HCl pH 8.5.

1.9 Selection of Plasmids

Primary selection was by analytical digestion assay, in which previously extracted vectors were incubated with restriction enzymes flanking the region of interest. The enzymes used for the ASRGL1 and ASRGL1_G10E genes were FastDigest™ NdeI and XhoI (Thermo Scientific) enzymes, with manufacturer's indicated buffer and reagent concentration. For the selection of plasmids the reactions were evaluated by agarose gel electrophoresis.

The selected plasmids were sequenced by the sequencing service of the Carlos Chagas Institute—FIOCRUZ/PR. The sequence used is Single Extension. After preparation of the sample by Macrogen (Korea) the sample is precipitated with ethanol and sequenced using Automatic Sequencer 3730xl. The result proved the identity of the human L-asparaginases contained in these clones.

Figure 5:
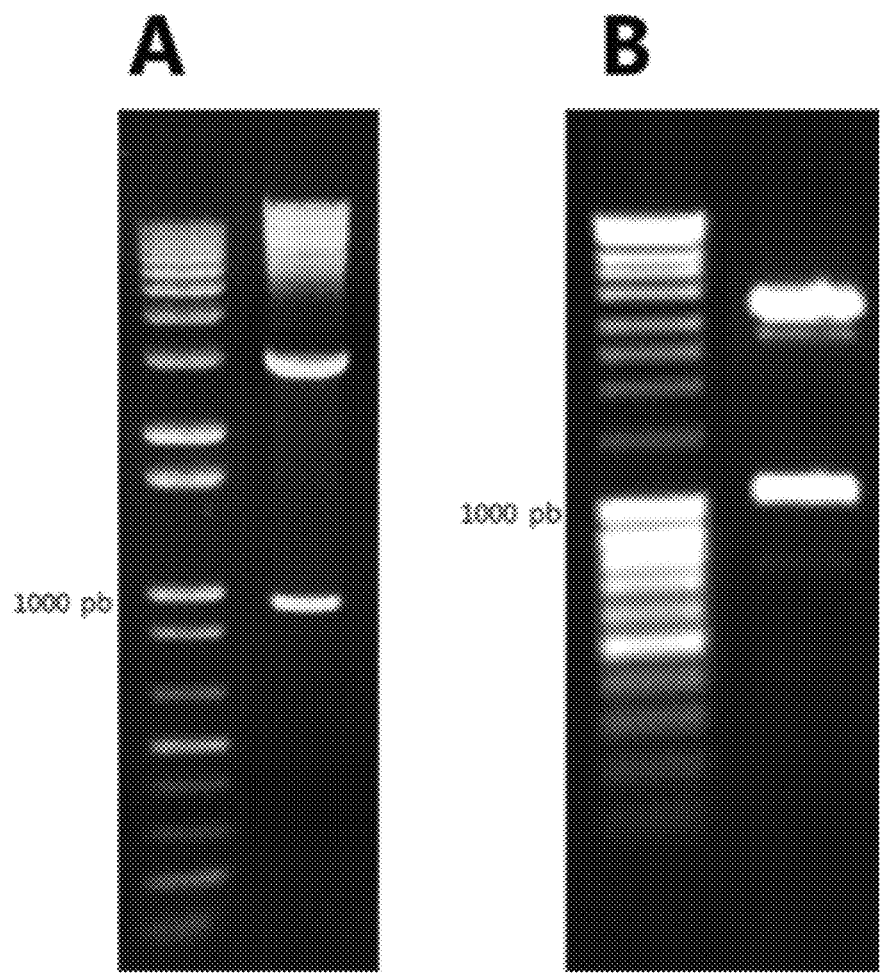
FIG. 5 shows the electrophoretic profile of the analytical digestion after cloning of ASRGL1 and ASRGL1_G10E PCR products in pGEM-T Easy.

FIG. 5 shows the electrophoretic profile of the analytical digestion after cloning of ASRGL1 and ASRGL1_G10E PCR products in pGEM-T Easy. In A, ASRGL1_pGEM-T Easy (insert with 944 pb) (M: 1 Kb Plus DNA Ladder, Invitrogen); and in B, ASRGL1_G10EpGEM-T Easy (insert with 944 pb) (M: MassRuler DNA Ladder Mix, Thermo Scientific).

1.10 Connecting Inserts to the Vector of Expression and Transformation

After the identity of the plasmid constructs (recombinant cloning vector containing the insert) sent to sequencing was confirmed, the preparatory digestion was performed in which the pGEM-T Easy vectors were incubated with the enzymes FastDigest™ NdeI and XhoI (Thermo Scientific) according to the manufacturer's indications. After agarose gel electrophoresis the inserts were purified by the QIAquick Gel Extraction Kit Protocol (QIAgen).

The purified inserts were subcloned in the expression vector pET28a-TEV. 2 U of T4 DNA Ligase (Invitrogen), 2 µL of 5× DNA Ligase Buffer (Invitrogen) and insert:plasmid in the ratio 1:1.5. The final volume was 10 µL and the reaction incubated for 16 hours at 4° C. The pET28a-TEV vector had previously been digested with the same enzymes. After connecting the insert in the vector, the transformation was done in the strain DH5α ({F-φ80lacZΔM15 Δ(lacZYA-argF) U169 recA1 endA1 hsdR17 (rk–, ink+) supE44 λ-thi-1 gyrA96 relA1 phoA}), following the thermal shock transformation protocol described in item 1.7. The confirmation of the expression vectors containing the inserts was also performed by analytical digestion followed by submission to sequencing.

Figure 6:
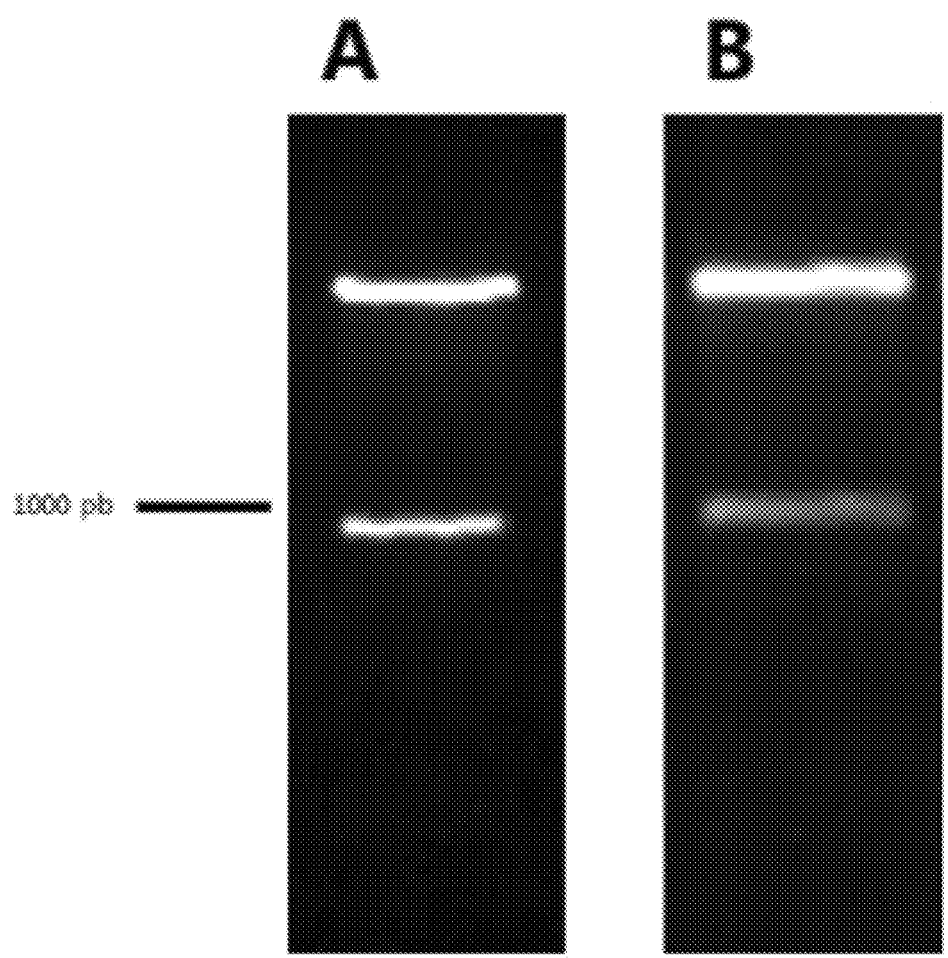
FIG. 6 shows the electrophoretic profile of the analytical digestion after subcloning in pET28a-TEV expression vector.

FIG. 6 shows the electrophoretic profile of the analytical digestion after subcloning in pET28a-TEV expression vector. In A, ASRGL1_pET28a-TEV (944 bp insert) and B, ASRGL1_G10E_pET28a-TEV (944 bp insert).

Example 2

Expression Test

ASRGL1-pET28a-TEV and ASRGL1_G10E-pET28a-TEV expression vectors were used to transform E. coli BL21 Star (DE3; {F-ompT hsdSB (rB–, mB–) galdcmrne131 (DE3)}) and/or E. coli C43 (DE3; {F-ompT hsdSB (rB–, mB–) galdcm (DE3)}) strains and thus test the expression at temperatures of 37, 30 and 20° C.

The BL21 Star (DE3) strain, derived from the strain used for ASRGL1 expression by Cantor et al (2009), is indicated for high levels of expression based on vectors regulated by the T7 promoter (such as pET28a-TEV). This is because they have a mutation in the rne131 gene that encodes for the enzyme RNase E, an endonuclease that participates in the degradation of mRNA. The mutation in the gene of this endonuclease allows greater stability to the transcribed mRNA, thus, an increase in the expression of the protein of interest (GRUNBERG-MANAGO et al, 1999).

The E. coli C43 (DE3) strain was also tested for compliance with the protocol described by Nomme et al (2012). This is a strain effective in expressing toxic proteins from all organisms, including mammals. The activity level of T7 RNAP is reduced through a mutation, thus reducing cell death associated with over-expression of many toxic proteins (DUMON-SEGNOVERT et al, 2004).

One isolated colony was grown for 16 hours at 37° C. under agitation of 200 rpm in 5 mL of LB medium containing kanamycin (25 µg/ml). After this period, a dilution (1:100) was performed and the culture was grown at 37° C. until the log growth phase was reached (D.O.600 0.8). At this point, an aliquot was separated, and the culture was induced with 0.5 mM isopropyl-β-D-tiogalactopyranoside (IPTG) inductor. The incubation was continued for 4 hours at 37° C., 30° C. and 20° C. For the test the temperature of 20° C. the culture was induced with IPTG only when reaching D.O.600 1,2.

The cells were collected by centrifugation at 6,000×g for 15 minutes at 4° C. and resuspended in 1 mL of Buffer A (TrisHCl 50 mM pH 7.4, NaCl 300 mM). After 30 minutes incubation with lysozyme (10 µg/mL) The lysis was done by sonication, giving 2 pulses of 15 seconds with an interval of 30 seconds (Ultrasonic Processor 500, Cole Panner). After centrifugation for 30 minutes at 20,000×g at 4° C. the pellet and supernatant were separated, referring to the insoluble and soluble fractions respectively. The pellet was resuspended in 1 mL of Buffer A with the addition of 8 M urea. For polyacrylamide gel electrophoresis (SDS-Page) 5 µL protein sample buffer 4× to 15 µL aliquot removed in each pass (total extract and, after centrifugation, pellet and supernatant, corresponding to the insoluble and soluble fractions respectively), incubating at 95° C. for 5 minutes for application in gels prepared by the traditional protocol (LAE-MIVILI, 1970). The prepared samples were applied in separator gels (13% bisacrylamide) and concentrator (5% bisacrylamide). The molecular weight marker used was Precision Plus Protein™ Unstained Standards (BioRad).

Example 3

Self-Processing Test

3.1 Expression and Purification by Nickel Resin

For the evaluation of the auto cleavage efficiency of recombinant proteins the expression in E. coli BL21 Star (DE3; {F-ompT hsdSB (rB–, mB–) galdcmrne131 (DE3)} was performed) An isolated colony was inoculated in 5 mL of LB medium containing 25 µg/mL of canaminicin. After growth for 16 hours at 37° C. and 200 rpm, a 1:100 dilution of this culture was performed in 500 mL of LB medium plus 25 µg/mL of canaminicin. The growth of the crop to the exponential growth phase (D.O.600 0.8) occurred under agitation of 200 rpm at 37° C. Then 0.5 mM of IPTG inductor was added and growth continued for another 4 hours under the same conditions.

The cultures were centrifuged at 6,000×g for 15 minutes at 4° C. and suspended in Buffer A with the addition of 10 mg/ml of lysozyme. After a 30-minute incubation on ice, lysis was performed through 8 sonication cycles with 30-second pulses and 60-second intervals. Pellet and supernatant were separated as insoluble and soluble fraction, respectively, by centrifugation at 20,000×g for 30 minutes at 4° C.

The soluble fractions were purified in nickel resin (Ni-NTA Superflow, QIAgen) through the following steps: incubation of the soluble fraction with the nickel resin for 1 hour under stirring; centrifugation and removal of the supernatant (called Flow through, as it corresponds to the fraction that did not bind to the column); washing by incubation with Buffer A plus 50 mM imidazole; centrifugation and removal of the supernatant (elution with 50 mM imidazole); washing by incubation with Buffer A plus 100 mM imidazole; centrifugation and removal of the supernatant (elution with 100 mM imidazole)elution with Buffer B (TrisHCl 50 mM pH 7.4, NaCl 300 mM, Imidazole 500 mM); centrifugation and removal of supernatant (elution with 500 mM imidazole). Flow through and elution fractions were evaluated by SDS-Page 13% electrophoresis.

3.2 Western Blot

The efficiency of the self-processing was verified by visualizing the bands corresponding to each state in the Western blot technique (TOWBIN et al., 1979). Initially the samples were submitted to SDS-Page gel electrophoresis of 13%. After electrophoresis, the proteins were transferred for 50 minutes at 20 V to a PVDF membrane, previously sensitized with 100% methanol, in Semidry system. Once the transfer was completed, the membrane was stained with Ponceau's solution to check the quality of the transfer and, then decorated with water for incubation for 30 minutes with blocking solution at room temperature. After this period, three 5-minute washes were performed with PBS-TWEEN 20 Buffer.

The membrane containing the proteins was then incubated in PBS-TWEEN 20 Buffer (PBS-Tween 20 0.1%) containing the primary antibody (anti-his) at dilution 1:3,000. This incubation was performed under agitation at 4° C. for 2 hours. After the washing steps as described above, the membrane was incubated with the secondary antibody (peroxidase-conjugated anti-mouse, Sigma) at a dilution of 1:10,000 in PBS Buffer-TWEEN 20 for 1 hour under stirring at 4° C.

The membrane was then washed again for chemiluminescence disclosure. The luminol and peroxidase solution in the 1:1 portion (SuperSignal™ West Pico Chemiluminescent Substrate, Thermo Scientific) was distributed on the membrane according to the manufacturer's indications and revealed through exposures of 5 to 20 minutes on the L-Pix Chemi Express photodocumenter (Loccus) through the L-Pix Image Software.

Example 4

Expression and Purification of Recombinant Proteins 4.1 Expression

The large-scale expression of ASRGL1 and ASRGL1_G10E in *E. coli* BL21 Star (DE3; {F-ompT hsdSB (rB−, mB−) galdcmrne131 (DE3)}) was performed as follows: One isolated colony was grown for 16 hours at 37° C. under agitation of 200 rpm in 5 mL of LB medium containing kanamycin (25 μg/ml). After this period, a dilution (1:100) was performed and the culture was grown at 37° C. until the log growth phase was reached (D.O.600 0.8). At this point, an aliquot was separated, and the culture was induced with 0.5 mM isopropyl-β-D-tiogalactopyranoside (IPTG) inductor. The incubation was continued for 4 hours at 37° C. The cells were collected by centrifugation at 6,000×g for 15 minutes at 4° C.

4.2 Sample Preparation

After resuspension of the pellets in C Buffer (TrisHCl 50 mM pH 7.4, NaCl 300 mM), lysis was performed through 8 to 12 passages under a pressure of 80 psi in a microfluidizer (M-110L Microfluidizer®), Microfluidics) followed by centrifugation at 20,000×g for 30 minutes at 4° C. The soluble fractions were reserved for purification.

4.3 ASRGL1 Purification 4.3.1 Affinity Chromatography

The expression vector pET28a-TEV allows the recombinant protein to be expressed fused to an N-terminal histidine tail, which makes it possible to use chromatography columns containing immobilized solid phase nickel for the purification process, since the histidine tail has an affinity for this metal. For this chromatographic method, the buffers C (TrisHCl 50 mM pH 7.4, NaCl 300 mM) and D (TrisHCl 50 mM pH 7.4, NaCl 300 mM, Imidazole 1M).

Nickel column affinity chromatography was performed in the Äkta system (Äkta Pure M25 or Äkta Purifier UPC 100, GE Healthcare) FPLC (Fast Performance Liquid Chromatography), Amersham Bioscience) in column HisTrap HP 1 mL (GE Healthcare). The column was first balanced in C buffer (TrisHCl 50 mM pH 7.4, NaCl 300 mM). The sample was then injected, and the column was rinsed with C buffer to remove the unbound proteins. During purification, a 0-100% gradient of D buffer (TrisHCl 50 mM pH 7.4, NaCl 300 mM, Imidazole 1M) was used for the elution of proteins in 20 column volumes, since imidazole competes with histidine for the binding to Nickel immobilized in the column. Depending on the amplitude of the absorbance signal, the D-buffer gradient was retained to improve the separation efficiency in chromatography. The fractions from the chromatography were collected with a flow of 1 mL per minute and analyzed through SDS-Page. The fractions containing the protein of interest in its purest form were joined and concentrated by centrifugation at 3,000×g using Amicon Ultra 10 (10000 MWCO) filters, Millipore).

4.3.2 Ion Exchange Chromatography

To achieve a higher purity level of ASRGL1 samples, HiTrap Q FF (GE Healthcare) column ion exchange chromatography was required. For this purpose, the samples were diluted 10× in E buffer (TrisHCl 50 mM pH 7.4) to reduce the salt concentration. The pH 7.4 of buffer E was chosen considering the positive resin charge and noting that the theoretical pI of ASRGL1 is equal to 6.27 (ExPASy ProtParam software), when the protein will then find itself negatively charged (anionic exchange) enabling efficient interaction with the column.

In Äkta FPLC system the column was balanced in E-buffer and after injection the sample was washed with E-buffer. The elution occurred in 20 column volumes through a 0-100% F buffer gradient (TrisHCl 50 mM pH 7.4, NaCl 1 M), whose high salt concentration promotes the decoupling of proteins from the column. Again, retention was used in the gradient according to absorbance. The fractions containing the protein of interest in its purest form were united and concentrated by centrifugation at 3,000×g using Amicon Ultra 10 filters (10000 MWCO, Millipore).

4.3.3 Filtration Gel Chromatography

For complete removal of contaminants, the ASRGL1 fractions concentrated in the previous chromatographic step were subjected to gel chromatography filtration using Superdex 75 10/300 GL (GE Healthcare) column in Äkta FPLC system. The sample volume applied varied between 320 and 450 μL and the elution of the wild protein was done in 1.5 volumes of G buffer column (TrisHCl 50 mM pH 7.4, NaCl 180 mM) or H (TrisHCl 50 mM pH 7.4, NaCl 470 mM) according to the salt concentration observed in ion exchange chromatography, with flow rate of 0.5 mL per minute. Filtration gel chromatography is a method of macromolecule analysis and which consists of separating biomolecules according to their size and shape. The column in this process contains a polymer with defined pore size cross-links. The larger molecules will migrate faster than the smaller ones, because they are not able to penetrate the interior of the resin pores, eluted directly from the column. The smaller molecules, by entering through the pores of the column, and take longer to go through the pores, are eluted late from the larger molecules.

4.4 ASRGL1_G10E Purification 4.1 Affinity Chromatography

ASRGL1_G10E affinity chromatography was performed in Äkta FPLC system in HisTrap HP 1 mL column (GE Healthcare). The column was first balanced in C buffer. The sample was then injected, and the column was washed with C buffer ((TrisHCl 50 mM pH 7.4, NaCl 300 mM) to remove the unbound proteins. Two elution steps were performed, the first in 10 column volumes with a 0-15% gradient of D buffer (TrisHCl 50 mM pH 7.4, NaCl 300 mM, Imidazol 1M), and the second step with 15-100% D buffer in 10 column volumes.

The fractions of interest were united and concentrated, but because they showed consistent presence of contaminants a second affinity chromatography was performed, using the same methodology. Only the first elution step was changed, in which there was an increase to 20 column volumes. The resulting fractions were analyzed by SDS-Page and Western blot, followed by concentration by centrifugation.

4.2 Ion Exchange Chromatography

The ion exchange chromatography of ASRGL1_G10E presented the same anionic character of the chromatography performed with ASRGL1, because at pH 7.4 of E ASRGL1_G10E buffer (pI 5.81) is negatively charged. The methodology used was the same as described in section 3.8.3.2, including sample preparation for application in the HiTrap Q FF column (GE Healthcare). The fractions from this chromatography were individually concentrated for use in the tests described in Examples 5 and 6.

Example 5

Enzymatic Assays

The kinetic activity of enzymes was evaluated by the AHA assay (FRAER; BURREL, 1955; VERMA, 2005; LI et al., 2012).

Reactions with the enzymes ASRGL1 and ASRGL1_G10E were performed with 0.004 mg of each fraction, 10 µL of AHA solution (AHA 10 mM) and sufficient amount of the reaction buffer for a total volume of 200 µL. The reactions were incubated at 37° C. for 10 minutes followed by the addition of TCA solution to stop the reaction. After adding 1000 µL of Oxin solution the samples were heated to 95° C. for 1 minute and then cooled for 10 minutes at 4° C. for subsequent reading at 705 nm (Synergy H1 Hybrid Reader, BioTek).

The absorbance values obtained were converted into µmols of aspartate generated in the reaction through the equation:

$$\mu mol \text{ of aspartate in reaction} = \left(\frac{DO_{705}}{1.77 \cdot 10^4}\right) \cdot 0.26 \cdot 10^6$$

The amount of aspartate generated in the reaction is then converted into experimental enzymatic activity (µmols of aspartate generated by mL of enzyme) by the equation:

Enzyme activity experiment =

$$\frac{\mu mol \text{ of aspartate in reaction}}{\text{Enzyme volume} \cdot \text{reaction time} \cdot \text{total volume of the reaction}}$$

To calculate the kcat values of each fraction the reaction speed is divided by the total concentration of enzyme in the reaction, where the speed is calculated by dividing the quantity in µmols of aspartate generated in the reaction by the total reaction time in seconds.

The kinetic parameters for AHA hydrolysis of the ASRGL1 and ASRGL1_G10E fractions are as shown in Table 3 below.

TABLE 3

Kinetic parameters of AHA hydrolysis of ASRGL1 and ASRGL1_G10E fractions. The values of experimental enzymatic activity can be found at µmols of aspartate generated by ml of enzyme.

| Sample | Kcat (s−1) | Experimental enzyme activity |
|---|---|---|
| ASRGL1_inactive_a | 0.1 ± 0.05 | 5.87 ± 2.94 |
| ASRGL1_inactive_b | 0.13 ± 0.04 | 7.83 ± 2.61 |
| ASRGL1_active | 0.32 ± 0.12 | 9.55 ± 3.67 |
| ASRGL1_G10E_active_a | 4.73 ± 0.13 | 143.95 ± 3.92 |
| ASRGL1_G10E_active_b | 3.35 ± 0.07 | 101.85 ± 2.28 |

Example 6

Differential Scanning Fluorimetry

Each fraction of the wild and mutant proteins was diluted at 2 µM in the elution buffer of the last chromatographic step and dispensed in a 96-well (Axygen) PCR microplate. 200× of SYPRO Orange (SYPRO® Orange protein gel stain, Life Technologies) have been added to each well for a final volume of 25 µL. Each fraction was tested in triplicate. The plates were sealed with an adhesive seal (Adhesive PCR Film, Thermo Scientific) to prevent any evaporation. The experiment was conducted on a Real-Time 7500 PCR machine (Applied Biosystems).

The determination of the TM of each fraction was performed through the OriginProB software. For this, the data were adjusted by Boltzmann's sigmoidal regression model, where the point of inflection represents the TM.

REFERENCES

1. DOLOWY, W. C., HEMNSON, D., CORNET, J., SELLIN, H. Toxic and antineoplastic effects of L-asparaginase. *Cancer* 19, 1813-1819 (1966).
2. Hill, J. M. et al. L-asparaginase therapy for leukemia and other malignant neoplasms. *JAMA J. Am. Med. Assoc.* 202, 882-8 (1967).
3. Pejovic, T. & Schwartz, P. E. Leukemias. *Clin. Obstet. Gynecol.* 45, 866-878 (2002).
4. INCA. Instituto Nacional de Câncer José Alencar Gomes da Silva. Estimativa 2016: Incidência de Câncer no Brasil. *Ministério da Saúde* (2015). Available at: http://www.inca.gov.br. (Accessed: 1st July 2016)
5. Rose-Inman, H. & Kuehl, D. Acute leukemia. *Emerg. Med. Clin. North Am.* 32, 579-96 (2014).
6. Avramis, V. I. Asparaginases: Biochemical pharmacology and modes of drug resistance. *Anticancer Res.* 32, 2423-2437 (2012).
7. Instituto Nacional de Cancer José Alencar Gomes da Silva. *INCA—Instituto Nacional de Cancer—Estimativa 2016. Ministério da Saúde Instituto Nacional de Cancer José Alencar Gomes da Silva* (2016). doi:978-85-7318-283-5
8. Moghrabi, A. et al. Results of the Dana-Farber Cancer Institute ALL Consortium Protocol 95-01 for children with acute lymphoblastic leukemia. *Blood J.* 109, 896-905 (2007).

9. Carroll, W. L. et al. Pediatric acute lymphoblastic leukemia. *Hematol. Am Soc Hematol Educ Program* 102-131 (2003). doi:10.1182/ asheducation-2010.1.363
10. Cooper, S. L. & Brown, P. A. Treatment of pediatric acute lymphoblastic leukemia. *Pediatr. Clin. North Am.* 62, 61-73 (2015).
11. Hunger, S. P. et al. Improved survival for children and adolescents with acute lymphoblastic leukemia between 1990 and 2005: A report from the children's oncology group. *J. Clin. Oncol.* 30, 1663-1669 (2012).
12. American Cancer Society. Cancer Facts & FIGS. 2014. *Cancer Facts Fig.* 1-72 (2014). doi:10.1177/0300985809357753
13. Richards, N. G. J. & Kilberg, M. S. Asparagine synthetase chemotherapy. *Annu. Rev. Biochem.* 75, 629-54 (2006).
14. Li, B. S. et al. The downregulation of asparagine synthetase expression can increase the sensitivity of cells resistant to 1-asparaginase. *Leukemia* 20, 2199-201 (2006).
15. Song, P. et al. Asparaginase induces apoptosis and cytoprotective autophagy in chronic myeloid leukemia cells. *Oncotarget* 6, 3861-73 (2015).
16. Li, B. S. et al. The downregulation of asparagine synthetase expression can increase the sensitivity of cells resistant to L-asparaginase. *Leukemia* 20, 2199-2201 (2006).
17. Pieters, R., Hunger, S. P., Boos, J., Rizzari, C. & Pui, C. L-asparaginase treatment in acute lymphoblastic leukemia: a focus on Erwinia asparaginase. *Cancer* 117, 238-249 (2011).
18. Ueno, T. et al. Cell cycle arrest and apoptosis of leukemia cells induced by L-asparaginase. *Leukemia* 11, 1858-61 (1997).
19. Yu, M. et al. L-asparaginase inhibits invasive and angiogenic activity and induces autophagy in ovarian cancer. 16, 2369-2378 (2012).
20. Willems, L. et al Inhibiting glutamine uptake represents an attractive new strategy for treating acute myeloid leukemia Inhibiting glutamine uptake represents an attractive new strategy for treating acute myeloid leukemia. 122, 3521-3532 (2013).
21. Zhang, B. et al. Targeting asparagine and autophagy for pulmonary adenocarcinoma therapy. *Appl. Microbiol. Biotechnol.* 100, 9145-9161 (2016).
22. Lorenzi, P. L., Claerhout, S., Mills, G. B. & Weinstein, J. N. A curated census of autophagy-modulating proteins and small molecules. *Autophagy* 10, 1316-1326 (2014).
23. Panosyan, E. H. et al. Asparaginase depletion potentiates the cytotoxic effect of chemotherapy against brain tumors. *Mol Cancer Res* 12, 694-702 (2014).
24. Sircar, K. et al. Integrative molecular profiling reveals asparagine synthetase is a target in castration-resistant prostate cancer. *Am. J. Pathol.* 180, 895-903 (2012).
25. Kobrinsky, N. L. et al. Outcomes of Treatment of Children and Adolescents With Recurrent Non-Hodgkin's Lymphoma and Hodgkin's Chemotherapy, and Transplantation: Children's Cancer Group Study CCG-5912. *J. Clin. Oncol.* 19, 2390-2396 (2001).
26. Bansal, S. et al. Hyperthermophilic asparaginase mutants with enhanced substrate affinity and antineoplastic activity: structural insights on their mechanism of action. *FASEB J.* 26, 1161-1171 (2012).
27. Roth, G. et al. L-ASPARAGINASE II PRODUCTION IN *Escherichia coli* FED-BATCH CULTURES. *Braz. J. Chem. Eng.* 30, 245-256 (2013).
28. Rytting, M. E. Role of L-asparaginase in acute lymphoblastic leukemia: focus on adult patients. *Blood Lymphat. Cancer Targets Ther.* 2, 117-124 (2012).
29. Müller, H. J. & Boos, J. Use of L-asparaginase in childhood ALL. *Oncology/Hematology* 28, 97-113 (1998).
30. Patel, N. et al. A dyad of lymphoblastic lysosomal cysteine proteases degrades the antileukemic drug L-asparaginase. *J. Clin. Invest.* 119, 1964-1973 (2009).
31. Avramis, V. I. & Tiwari, P. N. Asparaginase (native ASNase or pegylated ASNase) in the treatment of acute lymphoblastic leukemia. *Int. J. Nanomedicine* 1, 241-254 (2006).
32. Oinonen, C., Tikkanen, R., Rouvinen, J. & Peltonen, L. Three-dimensional structure of human lysosomal aspartylglucosaminidase. *Nat. Struct. Biol.* 2, 1102-1108 (1995).
33. Sugimoto, H., Odani, S. & Yamashita, S. Cloning and expression of cDNA encoding rat liver 60-kDa lysophospholipase containing an asparaginase-like region and ankyrin repeat. *J. Biol. Chem.* 273, 12536-12542 (1998).
34. Cantor, J. R., Stone, E. M., Chantranupong, L. & Georgiou, G. The Human Asparaginase-Like Protein 1 hASRGL1 is an Ntn-Hydrolase with β-aspartyl Peptidase Activity. *Biochemistry (Mosc.)* 48, 11025-11031 (2009).
35. Böhme, L. et al. Isoaspartate residues dramatically influence substrate recognition and turnover by proteases. *Biol. Chem.* 389, 1043-1053 (2008).
36. Michalska, K. & Jaskólski, M. Structural aspects of 1-asparaginases, their friends and relations. *Acta Biochim. Pol.* 53, 627-640 (2006).
37. Dieterich, D. C. et al. Gliap) a novel untypical L-asparaginase localized to rat brain astrocytes. 1117-1125 (2003). doi:10.1046/ j.1471-4159.2003.01766. x
38. Evtimova, V., Zeillinger, R., Kaul, S. & Weidle, U. H. Identification of CRASH, a gene deregulated in gynecological tumors. *Int. J. Oncol.* 24, 33-41 (2004).
39. Brannigan, J. A. et al. A protein catalytic framework with an N-terminal nucleophile is capable of self-activation. *Nature* 378, 416-419 (1995).
40. Bush, L. A. N. N. et al. A Novel Asparaginase-Like Protein Is a Sperm Autoantigen in Rats. 247, 233-247 (2002).
41. Nomme, J., Su, Y., Konrad, M. & Lavie, A. Structures of apo and product-bound human L-asparaginase: Insights into the mechanism of autoproteolysis and substrate hydrolysis. *Biochemistry (Mosc.)* 51, 6816-6826 (2012).
42. Li, W. et al. Intramolecular Cleavage of the hASRGL1 Homodimer Occurs in Two Stages. *Biochemistry (Mosc.)* 55, 960-969 (2016).
43. Nomme, J., Su, Y. & Lavie, A. Elucidation of the specific function of the conserved threonine triad responsible for human 1-Asparaginase autocleavage and substrate hydrolysis. *J. Mol. Biol.* 426, 2471-2485 (2014).
44. Su, Y. et al. Free glycine accelerates the autoproteolytic activation of human asparaginase. *Chem. Biol.* 20, 533-540 (2013).
45. Li, W., Cantor, J. R., Yogesha, S. D., Yang, S. & Chantranupong, L. Uncoupling Intramolecular Processing and Substrate Hydrolysis in the N-terminal Nucleophile Hydrolase hASRGL1 by Circular Permutation. *ACS Chem. Biol.* 7, 1840-1847 (2012).
46. Karamitros, C. S. & Konrad, M. Bacterial co-expression of the alpha and beta protomers of human 1-asparaginase-3: Achieving essential N-terminal exposure of a catalytically critical threonine located in the beta-subunit. *Protein Expr. Purif.* 93, 1-10 (2014).
47. Schalk, A. M. & Lavie, A. Structural and Kinetic Characterization of Guinea Pig. *Biochemistry (Mosc.)* 53, 2318-2328 (2014).

SEQUENCE LISTING

<160> NUMBER OF SEQ ID NOS: 11

<210> SEQ ID NO 1
<211> LENGTH: 308
<212> TYPE: PRT
<213> ORGANISM: Homo sapiens

<400> SEQUENCE: 1

Met Asn Pro Ile Val Val His Gly Gly Ala Gly Pro Ile Ser
1               5                   10                  15

Lys Asp Arg Lys Glu Arg Val His Gln Gly Met Val Arg Ala Ala Thr
                20                  25                  30

Val Gly Tyr Gly Ile Leu Arg Glu Gly Gly Ser Ala Val Asp Ala Val
            35                  40                  45

Glu Gly Ala Val Val Ala Leu Glu Asp Pro Glu Phe Asn Ala Gly
    50                  55                  60

Cys Gly Ser Val Leu Asn Thr Asn Gly Glu Val Glu Met Asp Ala Ser
65                  70                  75                  80

Ile Met Asp Gly Lys Asp Leu Ser Ala Gly Ala Val Ser Ala Val Gln
                85                  90                  95

Cys Ile Ala Asn Pro Ile Lys Leu Ala Arg Leu Val Met Glu Lys Thr
            100                 105                 110

Pro His Cys Phe Leu Thr Asp Gln Gly Ala Ala Gln Phe Ala Ala Ala
        115                 120                 125

Met Gly Val Pro Glu Ile Pro Gly Glu Lys Leu Val Thr Glu Arg Asn
    130                 135                 140

Lys Lys Arg Leu Glu Lys Glu Lys His Glu Lys Gly Ala Gln Lys Thr
145                 150                 155                 160

Asp Cys Gln Lys Asn Leu Gly Thr Val Gly Ala Val Ala Leu Asp Cys
                165                 170                 175

Lys Gly Asn Val Thr Tyr Ala Thr Ser Thr Gly Gly Ile Val Asn Lys
            180                 185                 190

Met Val Gly Arg Val Gly Asp Ser Pro Cys Leu Gly Ala Gly Gly Tyr
        195                 200                 205

Ala Asp Asn Asp Ile Gly Ala Val Ser Thr Thr Gly His Gly Glu Ser
    210                 215                 220

Ile Leu Lys Val Asn Leu Ala Arg Leu Thr Leu Phe His Ile Glu Gln
225                 230                 235                 240

Gly Lys Thr Val Glu Glu Ala Ala Asp Leu Ser Leu Gly Tyr Met Lys
                245                 250                 255

Ser Arg Val Lys Gly Leu Gly Gly Leu Ile Val Val Ser Lys Thr Gly
            260                 265                 270

Asp Trp Val Ala Lys Trp Thr Ser Thr Ser Met Pro Trp Ala Ala Ala
        275                 280                 285

Lys Asp Gly Lys Leu His Phe Gly Ile Asp Pro Asp Asp Thr Thr Ile
    290                 295                 300

Thr Asp Leu Pro
305

<210> SEQ ID NO 2
<211> LENGTH: 1332
<212> TYPE: DNA
<213> ORGANISM: Homo sapiens

<400> SEQUENCE: 2
cggggagcgg cggtaccggg cggctgcggg gctggctcga cccagcttga ggtctcggcg    60

```
tccgcgtcct gcggtgccct gggatccgcc gacatgaatc ccatcgtagt ggtccacggc    120
ggcggagccg gtcccatctc caaggatcgg aaggagcgag tgcaccaggg catggtcaga    180
gccgccaccg tgggctacgg catcctccgg gagggcggga gcgccgtgga tgccgtagag    240
ggagctgtcg tcgccctgga agacgatccc gagttcaacg caggttgtgg gtctgtcttg    300
aacacaaatg gtgaggttga atggatgct agtatcatgg atggaaaaga cctgtctgca     360
ggagcagtgt ccgcagtcca gtgtatagca aatcccatta aacttgctcg gcttgtcatg    420
gaaaagacac ctcattgctt tctgactgac caaggcgcag cgcagtttgc agcagctatg    480
ggggttccag agattcctgg agaaaaactg gtgacagaga gaaacaaaaa gcgcctggaa    540
aaagagaagc atgaaaaagg tgctcagaaa acagattgtc aaaaaaactt gggaaccgtg    600
ggtgctgttg ccttggactg caagggaat gtaacctacg caacctccac aggcggtatc     660
gttaataaaa tggtcggccg cgttgggac tcaccgtgtc taggagctgg aggttatgcc     720
gacaatgaca tcggagccgt ctcaaccaca gggcatgggg aaagcatcct gaaggtgaac    780
ctggctagac tcaccctgtt ccacatagaa caaggaaaga cggtagaaga ggctgcggac    840
ctatcgttgg gttatatgaa gtcaagggtt aaaggtttag gtggcctcat cgtggttagc    900
aaaacaggag actgggtggc aaagtggacc tccacctcca tgccctgggc agccgccaag    960
gacggcaagc tgcactttgg aattgatcct gacgatacta ctatcaccga ccttccctaa   1020
gccgctggaa gattgtattc cagatgctag cttagaggtc aagtacagtc tcctcatgag   1080
acatagccta atcaattaga tctagaattg gaaaaattgt cccgtctgtc acttgttttg   1140
ttgccttaat aagcatctga atgtttggtt gtggggcggg ttttgaagcg atgagagaaa   1200
tgcccgtatt aggaggatta cttgagccct ggaggtcaaa gctgaggtga gccatgatta   1260
ctccactgca ctccagcctg gcaacagag ccaggccctg tatcaaaaaa aaaaaaaaaa    1320
aaaaaaaaaa aa                                                      1332
```

<210> SEQ ID NO 3
<211> LENGTH: 308
<212> TYPE: PRT
<213> ORGANISM: Artificial Sequence
<220> FEATURE:
<223> OTHER INFORMATION: Substitution of G with E in position 10 of the wild sequence

<400> SEQUENCE: 3

```
Met Asn Pro Ile Val Val His Gly Glu Gly Ala Gly Pro Ile Ser
1               5                   10                  15

Lys Asp Arg Lys Glu Arg Val His Gln Gly Met Val Arg Ala Ala Thr
                20                  25                  30

Val Gly Tyr Gly Ile Leu Arg Glu Gly Gly Ser Ala Val Asp Ala Val
            35                  40                  45

Glu Gly Ala Val Val Ala Leu Glu Asp Asp Pro Glu Phe Asn Ala Gly
        50                  55                  60

Cys Gly Ser Val Leu Asn Thr Asn Gly Glu Val Glu Met Asp Ala Ser
65                  70                  75                  80

Ile Met Asp Gly Lys Asp Leu Ser Ala Gly Ala Val Ser Ala Val Gln
                85                  90                  95

Cys Ile Ala Asn Pro Ile Lys Leu Ala Arg Leu Val Met Glu Lys Thr
            100                 105                 110

Pro His Cys Phe Leu Thr Asp Gln Gly Ala Ala Gln Phe Ala Ala Ala
        115                 120                 125
```

```
Met Gly Val Pro Glu Ile Pro Gly Glu Lys Leu Val Thr Glu Arg Asn
            130                 135                 140

Lys Lys Arg Leu Glu Lys Glu Lys His Glu Lys Gly Ala Gln Lys Thr
145                 150                 155                 160

Asp Cys Gln Lys Asn Leu Gly Thr Val Gly Ala Val Ala Leu Asp Cys
                165                 170                 175

Lys Gly Asn Val Thr Tyr Ala Thr Ser Thr Gly Gly Ile Val Asn Lys
                180                 185                 190

Met Val Gly Arg Val Gly Asp Ser Pro Cys Leu Gly Ala Gly Gly Tyr
                195                 200                 205

Ala Asp Asn Asp Ile Gly Ala Val Ser Thr Thr Gly His Gly Glu Ser
            210                 215                 220

Ile Leu Lys Val Asn Leu Ala Arg Leu Thr Leu Phe His Ile Glu Gln
225                 230                 235                 240

Gly Lys Thr Val Glu Glu Ala Ala Asp Leu Ser Leu Gly Tyr Met Lys
                245                 250                 255

Ser Arg Val Lys Gly Leu Gly Gly Leu Ile Val Val Ser Lys Thr Gly
                260                 265                 270

Asp Trp Val Ala Lys Trp Thr Ser Thr Ser Met Pro Trp Ala Ala Ala
                275                 280                 285

Lys Asp Gly Lys Leu His Phe Gly Ile Asp Pro Asp Asp Thr Thr Ile
            290                 295                 300

Thr Asp Leu Pro
305
```

<210> SEQ ID NO 4
<211> LENGTH: 308
<212> TYPE: PRT
<213> ORGANISM: Artificial Sequence
<220> FEATURE:
<223> OTHER INFORMATION: Substitution of G with D in position 10 of the
      wild sequence

<400> SEQUENCE: 4

```
Met Asn Pro Ile Val Val His Gly Asp Gly Ala Gly Pro Ile Ser
1               5                   10                  15

Lys Asp Arg Lys Glu Arg Val His Gln Gly Met Val Arg Ala Ala Thr
                20                  25                  30

Val Gly Tyr Gly Ile Leu Arg Glu Gly Gly Ser Ala Val Asp Ala Val
                35                  40                  45

Glu Gly Ala Val Val Ala Leu Glu Asp Asp Pro Glu Phe Asn Ala Gly
50                  55                  60

Cys Gly Ser Val Leu Asn Thr Asn Gly Glu Val Glu Met Asp Ala Ser
65                  70                  75                  80

Ile Met Asp Gly Lys Asp Leu Ser Ala Gly Ala Val Ser Ala Val Gln
                85                  90                  95

Cys Ile Ala Asn Pro Ile Lys Leu Ala Arg Leu Val Met Glu Lys Thr
                100                 105                 110

Pro His Cys Phe Leu Thr Asp Gln Gly Ala Ala Gln Phe Ala Ala Ala
                115                 120                 125

Met Gly Val Pro Glu Ile Pro Gly Glu Lys Leu Val Thr Glu Arg Asn
            130                 135                 140

Lys Lys Arg Leu Glu Lys Glu Lys His Glu Lys Gly Ala Gln Lys Thr
145                 150                 155                 160

Asp Cys Gln Lys Asn Leu Gly Thr Val Gly Ala Val Ala Leu Asp Cys
```

-continued

```
                       165                 170                 175
Lys Gly Asn Val Thr Tyr Ala Thr Ser Thr Gly Gly Ile Val Asn Lys
            180                 185                 190

Met Val Gly Arg Val Gly Asp Ser Pro Cys Leu Gly Ala Gly Gly Tyr
            195                 200                 205

Ala Asp Asn Asp Ile Gly Ala Val Ser Thr Thr Gly His Gly Glu Ser
            210                 215                 220

Ile Leu Lys Val Asn Leu Ala Arg Leu Thr Leu Phe His Ile Glu Gln
225                 230                 235                 240

Gly Lys Thr Val Glu Glu Ala Ala Asp Leu Ser Leu Gly Tyr Met Lys
            245                 250                 255

Ser Arg Val Lys Gly Leu Gly Gly Leu Ile Val Val Ser Lys Thr Gly
            260                 265                 270

Asp Trp Val Ala Lys Trp Thr Ser Thr Ser Met Pro Trp Ala Ala Ala
            275                 280                 285

Lys Asp Gly Lys Leu His Phe Gly Ile Asp Pro Asp Asp Thr Thr Ile
            290                 295                 300

Thr Asp Leu Pro
305

<210> SEQ ID NO 5
<211> LENGTH: 308
<212> TYPE: PRT
<213> ORGANISM: Artificial Sequence
<220> FEATURE:
<223> OTHER INFORMATION: Substitution of G with H in position 10 of the
      wild sequence

<400> SEQUENCE: 5

Met Asn Pro Ile Val Val His Gly His Gly Ala Gly Pro Ile Ser
1               5                   10                  15

Lys Asp Arg Lys Glu Arg Val His Gln Gly Met Val Arg Ala Ala Thr
            20                  25                  30

Val Gly Tyr Gly Ile Leu Arg Glu Gly Gly Ser Ala Val Asp Ala Val
            35                  40                  45

Glu Gly Ala Val Val Ala Leu Glu Asp Asp Pro Glu Phe Asn Ala Gly
            50                  55                  60

Cys Gly Ser Val Leu Asn Thr Asn Gly Glu Val Glu Met Asp Ala Ser
65                  70                  75                  80

Ile Met Asp Gly Lys Asp Leu Ser Ala Gly Ala Val Ser Ala Val Gln
            85                  90                  95

Cys Ile Ala Asn Pro Ile Lys Leu Ala Arg Leu Val Met Glu Lys Thr
            100                 105                 110

Pro His Cys Phe Leu Thr Asp Gln Gly Ala Ala Gln Phe Ala Ala Ala
            115                 120                 125

Met Gly Val Pro Glu Ile Pro Gly Glu Lys Leu Val Thr Glu Arg Asn
            130                 135                 140

Lys Lys Arg Leu Glu Lys Glu Lys His Glu Lys Gly Ala Gln Lys Thr
145                 150                 155                 160

Asp Cys Gln Lys Asn Leu Gly Thr Val Gly Ala Val Ala Leu Asp Cys
            165                 170                 175

Lys Gly Asn Val Thr Tyr Ala Thr Ser Thr Gly Gly Ile Val Asn Lys
            180                 185                 190

Met Val Gly Arg Val Gly Asp Ser Pro Cys Leu Gly Ala Gly Gly Tyr
            195                 200                 205
```

```
Ala Asp Asn Asp Ile Gly Ala Val Ser Thr Thr Gly His Gly Glu Ser
    210                 215                 220
Ile Leu Lys Val Asn Leu Ala Arg Leu Thr Leu Phe His Ile Glu Gln
225                 230                 235                 240
Gly Lys Thr Val Glu Glu Ala Ala Asp Leu Ser Leu Gly Tyr Met Lys
                245                 250                 255
Ser Arg Val Lys Gly Leu Gly Gly Leu Ile Val Val Ser Lys Thr Gly
            260                 265                 270
Asp Trp Val Ala Lys Trp Thr Ser Thr Ser Met Pro Trp Ala Ala Ala
        275                 280                 285
Lys Asp Gly Lys Leu His Phe Gly Ile Asp Pro Asp Asp Thr Thr Ile
    290                 295                 300
Thr Asp Leu Pro
305

<210> SEQ ID NO 6
<211> LENGTH: 1332
<212> TYPE: DNA
<213> ORGANISM: Artificial Sequence
<220> FEATURE:
<223> OTHER INFORMATION: Substitution of g with a in position 29 of the
      wild sequence

<400> SEQUENCE: 6
cggggagcgg cggtaccggg cggctgcgag gctggctcga cccagcttga ggtctcggcg     60
tccgcgtcct gcggtgccct gggatccgcc gacatgaatc ccatcgtagt ggtccacggc    120
ggcggagccg gtcccatctc caaggatcgg aaggagcgag tgcaccaggg catggtcaga    180
gccgccaccg tgggctacgg catcctccgg gagggcggga gcgccgtgga tgccgtagag    240
ggagctgtcg tcgccctgga agacgatccc gagttcaacg caggttgtgg gtctgtcttg    300
aacacaaatg gtgaggttga atggatgct agtatcatgg atggaaaaga cctgtctgca    360
ggagcagtgt ccgcagtcca gtgtatagca aatcccatta aacttgctcg gcttgtcatg    420
gaaaagacac ctcattgctt tctgactgac caaggcgcag cgcagtttgc agcagctatg    480
ggggttccag agattcctgg agaaaaactg gtgacagaga gaaacaaaaa gcgcctggaa    540
aaagagaagc atgaaaaagg tgctcagaaa acagattgtc aaaaaaactt gggaaccgtg    600
ggtgctgttg ccttggactg caaagggaat gtaacctacg caacctccac aggcggtatc    660
gttaataaaa tggtcggccg cgttggggac tcaccgtgtc taggagctgg aggttatgcc    720
gacaatgaca tcggagccgt ctcaaccaca gggcatgggg aaagcatcct gaaggtgaac    780
ctggctagac tcaccctgtt ccacatagaa caaggaaaga cggtagaaga ggctgcggac    840
ctatcgttgg gttatatgaa gtcaagggtt aaaggtttag gtggcctcat cgtggttagc    900
aaaacaggag actgggtggc aaagtggacc tccacctcca tgccctgggc agccgccaag    960
gacggcaagc tgcactttgg aattgatcct gacgatacta ctatcaccga ccttccctaa   1020
gccgctggaa gattgtattc cagatgctag cttagaggtc aagtacagtc tcctcatgag   1080
acatagccta atcaattaga tctagaattg gaaaaattgt cccgtctgtc acttgttttg   1140
ttgccttaat aagcatctga atgtttggtt gtggggcggg ttttgaagcg atgagagaaa   1200
tgcccgtatt aggaggatta cttgagccct ggaggtcaaa gctgaggtga gccatgatta   1260
ctccactgca ctccagcctg ggcaacagag ccaggccctg tatcaaaaaa aaaaaaaaaa   1320
aaaaaaaaaa aa                                                       1332
```

<210> SEQ ID NO 7
<211> LENGTH: 1331
<212> TYPE: DNA
<213> ORGANISM: Artificial Sequence
<220> FEATURE:
<223> OTHER INFORMATION: Deletion of g in position 28 of the wild
      sequence; substitution of g with a in position 30 of the wild
      sequence; substitution of g with t or c in position 31 of the wild
      sequence
<220> FEATURE:
<221> NAME/KEY: misc_feature
<222> LOCATION: (30)..(30)
<223> OTHER INFORMATION: n is t or c

<400> SEQUENCE: 7

```
cggggagcgg cggtaccggg cggctgcgan ctggctcgac ccagcttgag gtctcggcgt      60
ccgcgtcctg cggtgccctg ggatccgccg acatgaatcc catcgtagtg gtccacggcg     120
gcggagccgg tcccatctcc aaggatcgga aggagcgagt gcaccagggc atggtcagag     180
ccgccaccgt gggctacggc atcctccggg agggcgggag cgccgtggat gccgtagagg     240
gagctgtcgt cgccctggaa gacgatcccg agttcaacgc aggttgtggg tctgtcttga     300
acacaaatgg tgaggttgaa atggatgcta gtatcatgga tggaaaagac ctgtctgcag     360
gagcagtgtc cgcagtccag tgtatagcaa atcccattaa acttgctcgg cttgtcatgg     420
aaaagacacc tcattgcttt ctgactgacc aaggcgcagc gcagtttgca gcagctatgg     480
gggttccaga gattcctgga gaaaaactgg tgacagagag aaacaaaaag cgcctggaaa     540 agagaagca tgaaaaggt gctcagaaaa cagattgtca aaaaacttg ggaaccgtgg        600 gtgctgttgc cttggactgc aaagggaatg taacctacgc aacctccaca ggcggtatcg     660
ttaataaaat ggtcggccgc gttggggact caccgtgtct aggagctgga ggttatgccg     720
acaatgacat cggagccgtc tcaaccacag ggcatgggga agcatcctg aaggtgaacc       780 tggctagact caccctgttc cacatagaac aaggaaagac ggtagaagag gctgcggacc     840
tatcgttggg ttatatgaag tcaagggtta aaggtttagg tggcctcatc gtggttagca     900
aaacaggaga ctgggtggca agtggaccct ccacctccat gccctgggca gccgccaagg     960
acggcaagct gcactttgga attgatcctg acgatactac tatcaccgac cttccctaag    1020
ccgctggaag attgtattcc agatgctagc ttagaggtca agtacagtct cctcatgaga    1080
catagcctaa tcaattagat ctagaattgg aaaaattgtc ccgtctgtca cttgttttgt    1140
tgccttaata agcatctgaa tgtttggttg tggggcgggt tttgaagcga tgagagaaat    1200
gcccgtatta ggaggattac ttgagccctg gaggtcaaag ctgaggtgag ccatgattac    1260
tccactgcac tccagcctgg gcaacagagc caggccctgt atcaaaaaaa aaaaaaaaa    1320 aaaaaaaaa a                                                         1331
```

<210> SEQ ID NO 8
<211> LENGTH: 1332
<212> TYPE: DNA
<213> ORGANISM: Artificial Sequence
<220> FEATURE:
<223> OTHER INFORMATION: Substitution of g with c in position 28 of the
      wild sequence; substitution of g with a in position 29 of the wild
      sequence; substitution of g with t or c in position 30 of the wild
      sequence
<220> FEATURE:
<221> NAME/KEY: misc_feature
<222> LOCATION: (30)..(30)
<223> OTHER INFORMATION: n is t or c

<400> SEQUENCE: 8

```
cggggagcgg cggtaccggg cggctgccan gctggctcga cccagcttga ggtctcggcg    60
tccgcgtcct gcggtgccct gggatccgcc gacatgaatc ccatcgtagt ggtccacggc   120
ggcggagccg gtcccatctc caaggatcgg aaggagcgag tgcaccaggg catggtcaga   180
gccgccaccg tgggctacgg catcctccgg gagggcggga gcgccgtgga tgccgtagag   240
ggagctgtcg tcgccctgga agacgatccc gagttcaacg caggttgtgg gtctgtcttg   300
aacacaaatg gtgaggttga aatggatgct agtatcatgg atggaaaaga cctgtctgca   360
ggagcagtgt ccgcagtcca gtgtatagca aatcccatta aacttgctcg gcttgtcatg   420
gaaaagacac ctcattgctt tctgactgac caaggcgcag cgcagtttgc agcagctatg   480
ggggttccag agattcctgg agaaaaactg gtgacagaga gaaacaaaaa gcgcctggaa   540
aaagagaagc atgaaaaagg tgctcagaaa acagattgtc aaaaaaactt gggaaccgtg   600
ggtgctgttg ccttggactg caaagggaat gtaacctacg caacctccac aggcggtatc   660
gttaataaaa tggtcggccg cgttgggac tcaccgtgtc taggagctgg aggttatgcc    720
gacaatgaca tcggagccgt ctcaaccaca gggcatgggg aaagcatcct gaaggtgaac   780
ctggctagac tcaccctgtt ccacatagaa caaggaaaga cggtagaaga ggctgcggac   840
ctatcgttgg gttatatgaa gtcaagggtt aaaggtttag gtggcctcat cgtggttagc   900
aaaacaggag actgggtggc aaagtggacc tccacctcca tgccctgggc agccgccaag   960
gacggcaagc tgcactttgg aattgatcct gacgatacta ctatcaccga ccttccctaa  1020
gccgctggaa gattgtattc cagatgctag cttagaggtc aagtacagtc tcctcatgag  1080
acatagccta atcaattaga tctagaattg gaaaaattgt cccgtctgtc acttgttttg  1140
ttgccttaat aagcatctga atgtttggtt gtgggcggg ttttgaagcg atgagagaaa   1200
tgcccgtatt aggaggatta cttgagccct ggaggtcaaa gctgaggtga gccatgatta  1260
ctccactgca ctccagcctg ggcaacagag ccaggccctg tatcaaaaaa aaaaaaaaaa  1320
aaaaaaaaaa aa                                                     1332

<210> SEQ ID NO 9
<211> LENGTH: 24
<212> TYPE: DNA
<213> ORGANISM: Artificial Sequence
<220> FEATURE:
<223> OTHER INFORMATION: Initiator

<400> SEQUENCE: 9
catatgaatc ccatcgtagt ggtc                                           24

<210> SEQ ID NO 10
<211> LENGTH: 39
<212> TYPE: DNA
<213> ORGANISM: Artificial Sequence
<220> FEATURE:
<223> OTHER INFORMATION: Initiator

<400> SEQUENCE: 10
catatgaatc ccatcgtagt ggtccacggc gaaggagcc                           39

<210> SEQ ID NO 11
<211> LENGTH: 27
<212> TYPE: DNA
<213> ORGANISM: Artificial Sequence
```

```
<220> FEATURE:
<223> OTHER INFORMATION: Initiator

<400> SEQUENCE: 11
ctcgagttag ggaaggtcgg tgatagt                                              27
```

The invention claimed is:

1. A polypeptide with asparaginase activity, selected from the group consisting of:
   (i) a polypeptide that has an increased rate of auto-processing compared to a human wild type L-asparaginase and that has an amino acid sequence that is at least 90% identical to SEQ ID NO: 1 and which contains an amino acid substitution at a position corresponding to position 10 of SEQ ID NO: 1, wherein the amino acid is selected from the group consisting of glutamic acid, aspartic acid, histidine, arginine and lysine;
   (ii) a polypeptide comprising an amino acid sequence as set forth in SEQ ID NO: 1 except that the amino acid glycine at position 10 of SEQ ID NO: 1 is replaced by an amino acid selected from the group consisting of glutamic acid, aspartic acid and histidine;
   (iii) a polypeptide comprising an amino acid sequence set forth as any one of SEQ ID NOs: 3-5; and
   (iv) the polypeptide of any one of (i) to (iii) comprising one or more conservative amino acid substitutions.

2. The polypeptide according to claim 1, comprising an amino acid sequence set forth as SEQ ID NO: 3.

3. The polypeptide according to claim 1, comprising an amino acid sequence set forth as SEQ ID NO: 4.

4. The polypeptide according to claim 1, comprising an amino acid sequence set forth as SEQ ID NO: 5.

5. A polynucleotide comprising a nucleic acid sequence that encodes the polypeptide of claim 1.

6. The polynucleotide according to claim 5, wherein the nucleic acid sequence is set forth as any one of SEQ ID NOs: 6-8 or degenerations thereof.

7. An expression cassette comprising the polynucleotide of claim 5 operationally linked to a promoter and to a transcription terminator.

8. An expression vector comprising the expression cassette of claim 7.

9. The expression vector according to claim 8, wherein the polypeptide comprises an amino acid sequence set forth as SEQ ID NO: 3.

10. A host cell comprising the expression vector of claim 8.

11. A pharmaceutical composition comprising the polypeptide of claim 1 and a pharmaceutically acceptable carrier or excipient.

12. The pharmaceutical composition according to claim 11, wherein the composition is configured for intravenous administration.

13. The pharmaceutical composition according to claim 11, comprising an additional chemotherapeutic agent.

14. The pharmaceutical composition according to claim 11, wherein the polypeptide comprises an amino acid sequence set forth as SEQ ID NO: 3.

15. A method for producing a polypeptide with asparaginase activity, the method comprising:
   (a) providing the host cell of claim 10;
   (b) cultivating the host cell under conditions conducive to the production of the polypeptide encoded by the polynucleotide; and
   (c) isolating the produced polypeptide from cells or culture medium surrounding the host cell.

16. The method according to claim 15, wherein the polypeptide is labeled.

* * * * *